(12) United States Patent
Yu et al.

(10) Patent No.: US 11,717,248 B2
(45) Date of Patent: *Aug. 8, 2023

(54) SYSTEMS AND METHODS FOR IMAGE GENERATION

(71) Applicant: SHANGHAI UNITED IMAGING HEALTHCARE CO., LTD., Shanghai (CN)

(72) Inventors: Zhicong Yu, Houston, TX (US); Yuan Bao, Shanghai (CN); Dajun Wang, Shanghai (CN); Alexander Zamyatin, Cleveland, OH (US)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 235 days.

This patent is subject to a terminal disclaimer.

(21) Appl. No.: 17/215,114

(22) Filed: Mar. 29, 2021

(65) Prior Publication Data

US 2021/0212649 A1 Jul. 15, 2021

Related U.S. Application Data

(63) Continuation of application No. 16/236,595, filed on Dec. 30, 2018, now Pat. No. 10,959,695, which is a
(Continued)

(51) Int. Cl.
*A61B 6/00* (2006.01)
*A61B 6/03* (2006.01)
*G06T 11/00* (2006.01)

(52) U.S. Cl.
CPC ............ *A61B 6/5205* (2013.01); *A61B 6/032* (2013.01); *G06T 11/006* (2013.01); *G06T 11/008* (2013.01)

(58) Field of Classification Search
CPC ................ G06T 11/008; G06T 11/006; G06T 2211/424; G06T 2211/421; G06T 5/50;
(Continued)

(56) References Cited

U.S. PATENT DOCUMENTS 7,180,975 B2 2/2007 Heuscher et al.
7,751,524 B2 7/2010 Horiuchi et al.
(Continued)

FOREIGN PATENT DOCUMENTS

CN 105787973 A 7/2016

OTHER PUBLICATIONS

International Search Report in PCT/CN2018/107614 dated May 30, 2019, 4 pages.
(Continued)

*Primary Examiner* — Irakli Kiknadze
(74) *Attorney, Agent, or Firm* — Metis IP LLC

(57) ABSTRACT

The present disclosure relates to systems and methods for image generation. The methods may include obtaining projection data generated by a scanner; generating, based on a first weighting function, a first image by back-projecting the projection data, the first image having a first region corresponding to a first part of the object; generating, based on a second weighting function, a second image by back-projecting the projection data, the second image having a second region corresponding to the first part of the object, the second region of the second image presenting a better CT number uniformity than the first region of the first image; and generating a third image based on the first image and the second image.

20 Claims, 15 Drawing Sheets

Related U.S. Application Data continuation of application No. PCT/CN2018/107614, filed on Sep. 26, 2018.

(58) Field of Classification Search
CPC . G06T 2207/20221; G06T 2207/10081; G06T 2207/10104; G06T 2207/10088; G06T 2207/10132; G06T 2207/10108; G06T 5/003; G06T 2207/20172; G06T 2207/30004; G06T 2207/10072; G06T 7/0012; G06T 11/003; G06T 2210/41; G06T 2207/20084; G06T 19/20; G06T 17/00; G06T 2211/408; G06T 2219/2004; G06T 2211/436; G06T 2219/2021; G06T 11/005; G06T 2207/10116; G06T 2207/30012; G06T 2207/20081; G06T 2211/412; A61B 6/5205; A61B 6/032; A61B 6/5258; A61B 6/482; A61B 6/504; A61B 6/481; A61B 6/503; A61B 6/465; A61B 6/5217; A61B 6/42; A61B 6/467; A61B 6/4241; A61B 5/055; A61B 6/4291; A61B 8/488; A61B 8/5207; A61B 6/5235; A61B 6/487; A61B 6/4417; A61B 6/037; A61B 5/0035; A61B 6/4441; A61B 6/4085; A61B 6/025; A61B 6/502; A61B 6/0435; A61B 6/545; A61B 6/0414; A61B 6/4405; A61B 6/587; A61B 6/08; A61B 6/547; A61B 6/4452; A61B 2562/0233; A61B 2560/0487; A61B 6/06; A61B 6/461; A61B 6/542; A61B 6/40; A61B 6/54; A61B 6/548; A61B 6/588; A61B 6/4588; A61B 6/584; A61B 6/4429; A61B 6/589; A61B 6/488; A61B 6/4435; A61B 6/4208; A61B 6/4233; A61B 6/4266; A61B 6/469; A61B 6/0487; A61B 6/5282; A61B 6/4078; A61B 6/5264; A61B 6/50; A61B 6/405; A61B 6/03; A61B 6/583; A61B 6/0407; A61B 6/4275; A61B 6/582; A61B 6/5211; G06N 3/084; G06N 3/02; G06N 20/00; G06N 3/048; G06N 3/045; G06N 3/08; G01R 33/5608; G01R 33/543; G01R 33/5602; G01R 33/481; G01R 33/5616; G01R 33/561; G01R 33/56341; G01R 33/4835; A61N 5/1039; A61N 5/1045; A61N 5/1081; H04N 5/321; H04N 5/32; H04N 5/33; G01N 23/04; G01N 23/223; G01N 23/046; G21K 4/00; G21K 1/04; G21K 1/02; H05G 1/06; G01V 5/0008; G01V 5/0016; G01T 1/171; G16H 50/20
USPC .................................................. 378/4, 19, 62
See application file for complete search history.

(56) References Cited

U.S. PATENT DOCUMENTS

| | | | |
|---|---|---|---|
| 8,410,448 B2 | 4/2013 | Forthmann et al. | |
| 8,559,687 B2 | 10/2013 | Chiang et al. | |
| 10,959,695 B2 * | 3/2021 | Yu | G06T 11/008 |
| 2004/0146137 A1 * | 7/2004 | Bruder | A61B 6/032 |
| | | | 378/4 |
| 2009/0175562 A1 * | 7/2009 | Pan | A61B 6/5288 |
| | | | 382/312 |
| 2009/0238427 A1 | 9/2009 | Hsieh et al. | |
| 2010/0260404 A1 | 10/2010 | Ohishi | |
| 2012/0093281 A1 | 4/2012 | Zamyatin et al. | |
| 2014/0086466 A1 * | 3/2014 | Schwarz | G06T 7/0012 |
| | | | 378/4 |
| 2014/0326894 A1 * | 11/2014 | Abraham | G01N 23/046 |
| | | | 250/394 |
| 2015/0164464 A1 | 6/2015 | Mah et al. | |
| 2017/0086769 A1 * | 3/2017 | Allmendinger | A61B 6/482 |

OTHER PUBLICATIONS

Written Opinion in PCT/CN2018/107614 dated May 30, 2019, 4 pages.

Katsuyuki Taguchi et al., A New Weighting Scheme for Cone-beam Helical CT to Reduce the Image Noise, Physics Medicine and Biology, 49: 2351-2364, 2004.

D Heuscher et al., Redundant Data and Exact Helical Cone-beam Reconstruction, Physics in Medicine and Biology, 49: 2219-2238, 2004.

Rainer Grimmer et al., Cone-beam CT Image Reconstruction with Extended Z Range, Med. Phys, 36(7): 3363-3370, 2009.

Zhu, Lei et al., An Efficient Estimation Method for Reducing the Axial Intensity Drop in Circular Cone-Beam CT, International Journal of Biomedical Imaging, 2009, 11 pages.

Hu, Hui, An Improved Cone-Beam Reconstruction Algorithm for the Circular Orbit, Scanning, 18: 572-561, 1996.

Wang, Tonghe et al., Image-domain Non-uniformity Correction for Cone-beam CT, IEEE, 2017, 4 pages.

* cited by examiner

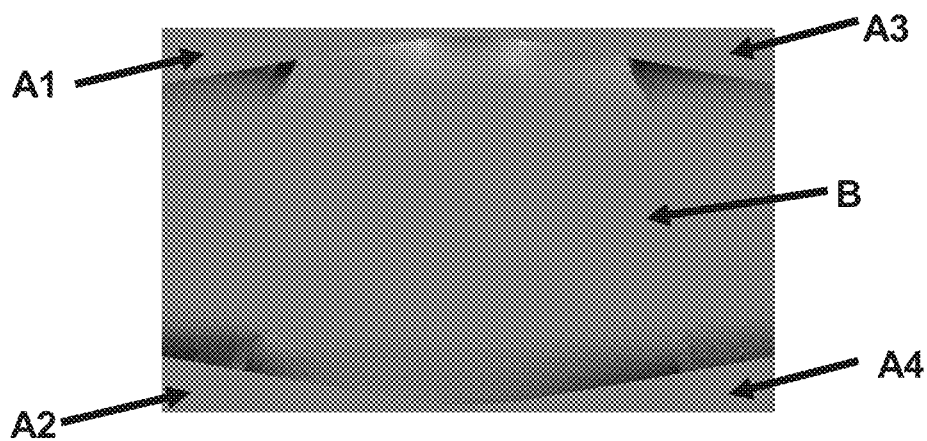
FIG. 13-A
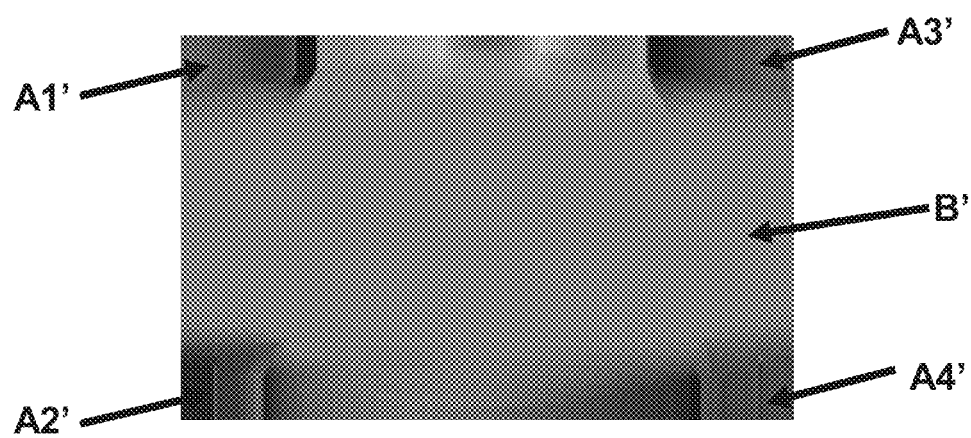
FIG. 13-B
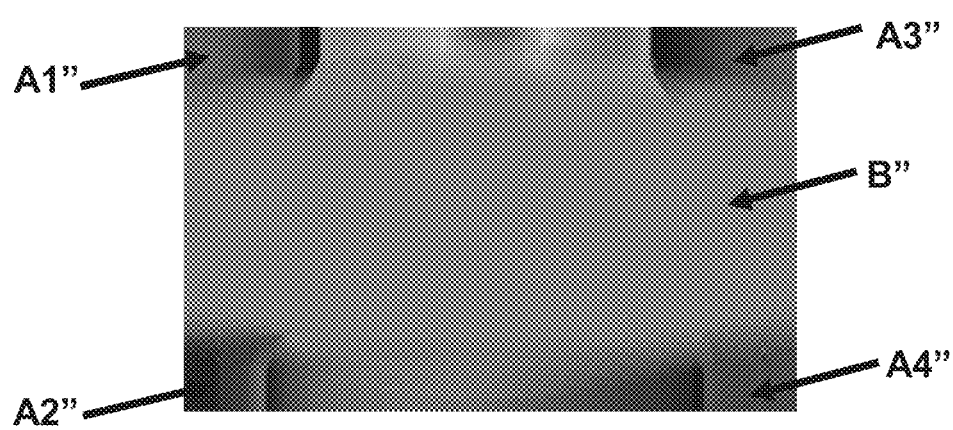
FIG. 13-C

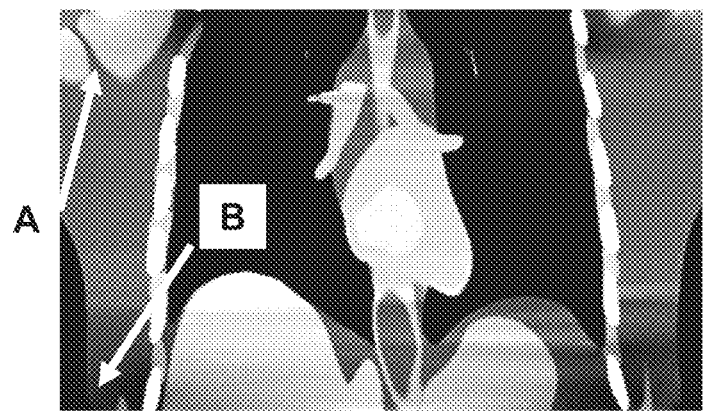
FIG. 14-A
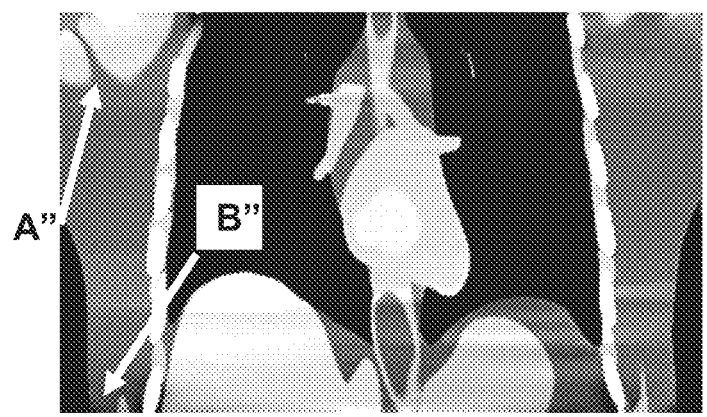
FIG. 14-B
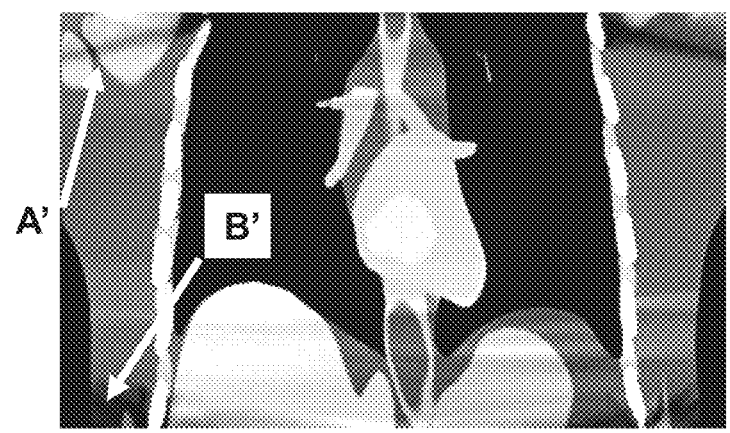
FIG. 14-C

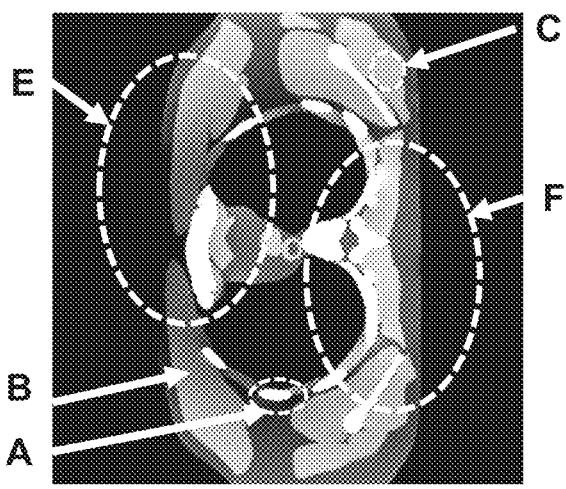
FIG. 15-A
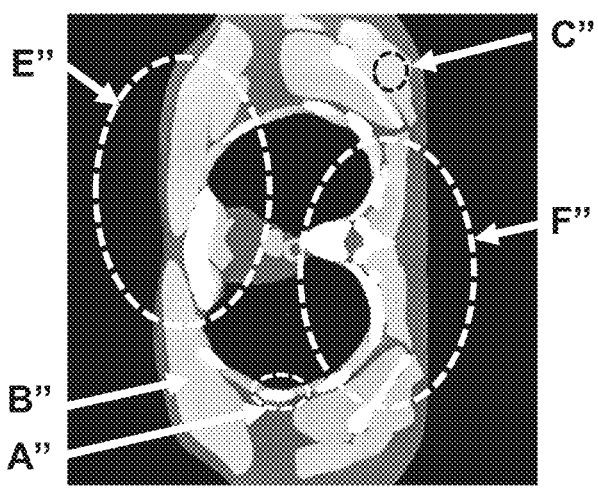
FIG. 15-B
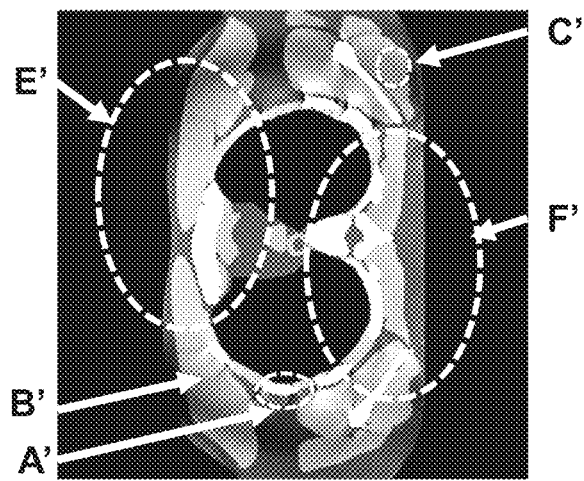
FIG. 15-C

SYSTEMS AND METHODS FOR IMAGE GENERATION

CROSS-REFERENCE TO RELATED APPLICATIONS

This present application is a continuation of U.S. application Ser. No. 16/236,595, filed on Dec. 30, 2018, which is a continuation of International Application No. PCT/CN2018/107614, filed on Sep. 26, 2018, designating the United States of America, the contents of which are hereby incorporated by reference.

TECHNICAL FIELD

The present disclosure generally relates to systems and methods for generating an image, and more specifically, to systems and methods for generating a computed tomography (CT) image with reduced artifacts.

BACKGROUND

Generally, a CT system may combine X-ray images taken from various angles to produce cross-sectional images, i.e., CT images, of an object. The quality of a CT image may be influenced by various factors, such as, the artifacts (e.g., cone beam artifacts) in the CT image, the CT number uniformity in the CT image, or the like. It is desirable to provide systems and method for generating a CT image with reduced artifacts and improved CT number uniformity.

SUMMARY

According to a first aspect of the present disclosure, a system is provided. The system may include at least one storage device that includes a set of instructions, and at least one processor in communication with the at least one storage device. When executing the instructions, the at least one processor may be configured to: cause the system to obtain projection data generated by a scanner; generate, based on a first weighting function, a first image by back-projecting the projection data, and the first image may have a first region corresponding to a first part of the object; generate, based on a second weighting function, a second image by back-projecting the projection data, the second image may have a second region corresponding to the first part of the object, and the second region of the second image may present a better CT number uniformity than the first region of the first image; and generate a third image based on the first image and the second image. The at least one processor may include a parallel hardware architecture having a plurality of processing threads, and the back projection of the projection data may be performed in parallel with respect to a voxel in the first image and a corresponding voxel in the second image.

In some embodiments, the first image may have fewer artifacts than the second image.

In some embodiments, the first image may include better high frequency components than the second image.

In some embodiments, the scanner may further include a radiation source configured to scan the object along a circular trajectory covering an angle range of 360° to produce the projection data.

In some embodiments, the first part of the object may be radiated by the radiation source at an angle range less than 360°, and the first region of the first image may include better low frequency components than the second region of the second image.

In some embodiments, to generate a third image, the at least one processor may be configured to cause the system to generate a difference image of the first image and the second image from each other by subtraction; and determine the third image based on the difference image and the first image.

In some embodiments, to determine the third image, the at least one processor may be configured to cause the system to generate a fourth image by performing a masking operation on the difference image; generate a fifth image by performing a data extrapolation operation on the fourth image; generate a sixth image by performing a low-pass filtering operation on the fifth image; and combine the sixth image and the first image to generate the third image.

In some embodiments, the first image may have a plurality of first voxels, to generate the first image, the at least one processor may be configured to cause the system to: for a first voxel of the plurality of first voxels, apply, according to the first weighting function, a weighting factor to first projection data corresponding to each of a plurality of projection angles to obtain weighted projection data of the first voxel; and back-project the weighted projection data of the first voxel to obtain back-projected data of the first voxel; and obtain the first image based on the back-projected data of the first voxel.

In some embodiments, the weighting factor applied to the first projection data corresponding to a projection angle may be associated with a first value of the first weighting function and a second value of the first weighting function; the first value of the first weighting function may be associated with a first projection point on a detector where radiation from the radiation source at the projection angle strikes; and the second value of the first weighting function may be associated with a second projection point on the detector where radiation from the radiation source at an opposite projection angle strikes.

In some embodiments, the parallel hardware architecture may include at least one graphic processing unit, and the at least one graphic processing unit may include a plurality of scalar processors.

According to a second aspect of the present disclosure, a method for image generation is provided. The method may be implemented on at least one machine each of which includes at least one processor and at least one storage device. The method may include: obtaining projection data generated by a scanner; generating, based on a first weighting function, a first image by back-projecting the projection data, the first image having a first region corresponding to a first part of the object; generating, based on a second weighting function, a second image by back-projecting the projection data, the second image having a second region corresponding to the first part of the object, the second region of the second image presenting a better CT number uniformity than the first region of the first image; and generating a third image based on the first image and the second image, wherein the at least one processor includes a parallel hardware architecture having a plurality of processing threads, and the back projection of the projection data are performed in parallel with respect to a voxel in the first image and a corresponding voxel in the second image.

According to a third aspect of the present disclosure, a non-transitory computer readable medium embodying a computer program product is provided. The computer program product may include instructions configured to cause a computing device to: obtain projection data generated by a scanner; generate, based on a first weighting function, a first image by back-projecting the projection data, and the first image may have a first region corresponding to a first part of the object; generate, based on a second weighting function, a second image by back-projecting the projection data, the second image may have a second region corresponding to the first part of the object, and the second region of the second image may present a better CT number uniformity than the first region of the first image; and generate a third image based on the first image and the second image. The at least one processor may include a parallel hardware architecture having a plurality of processing threads, and the back projection of the projection data may be performed in parallel with respect to a voxel in the first image and a corresponding voxel in the second image.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIG. 13-A is an exemplary image according to some embodiments of the present disclosure;

FIG. 13-B is an exemplary image generated based on a data extrapolation operation performed on FIG. 13-A according to some embodiments of the present disclosure;

FIG. 13-C is an exemplary image generated based on a low-filtering operation performed on FIG. 13-B according to some embodiments of the present disclosure;

FIGS. 14-A to 14-C illustrate three exemplary images according to some embodiments of the present disclosure; and FIGS. 15-A to 15-C illustrate three exemplary images according to some embodiments of the present disclosure.

DETAILED DESCRIPTION

The following description is presented to enable any person skilled in the art to make and use the present disclosure and is provided in the context of a particular application and its requirements. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown but is to be accorded the widest scope consistent with the claims.

The terminology used herein is for the purpose of describing particular exemplary embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," and/or "module" used herein are one method to distinguish different components, elements, parts, section or assembly of different level in ascending order. However, the terms may be displaced by another expression if they achieve the same purpose.

Figure 2:
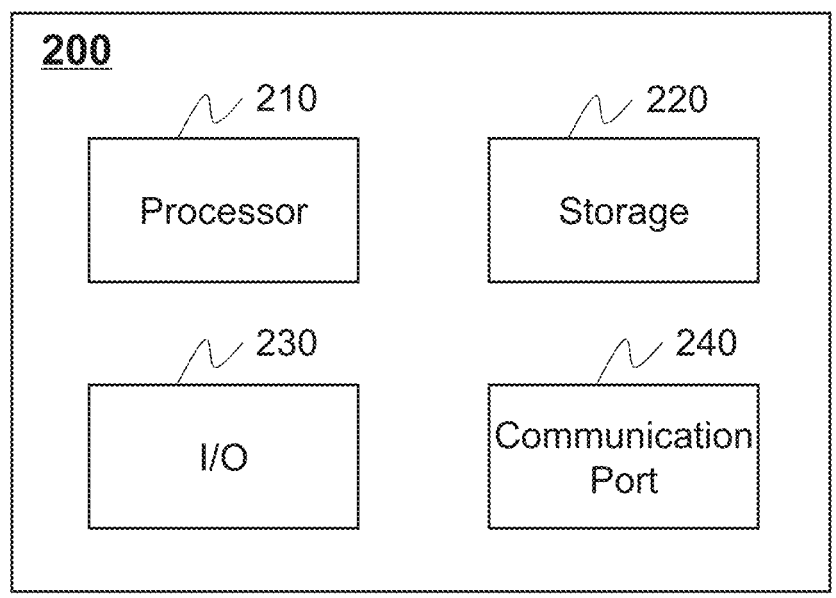
FIG. 2 is a schematic diagram illustrating exemplary hardware and/or software components of a computing device according to some embodiments of the present disclosure.

Generally, the word "module" or "unit" as used herein, refers to logic embodied in hardware or firmware, or to a collection of software instructions. A module or a unit described herein may be implemented as software and/or hardware and may be stored in any type of non-transitory computer-readable medium or another storage device. In some embodiments, a software module/unit may be compiled and linked into an executable program. It will be appreciated that software modules can be callable from other modules/units or from themselves, and/or may be invoked in response to detected events or interrupts. Software modules/units configured for execution on computing devices (e.g., processor 210 as illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units may be included in connected logic components, such as gates and flip-flops, and/or can be included of programmable units, such as programmable gate arrays or processors. The modules/units or computing device functionality described herein may be implemented as software modules/units, but may be represented in hardware or firmware. In general, the modules/units described herein refer to logical modules/units that may be combined with other modules/units or divided into sub-modules/sub-units despite their physical organization or storage. The description may be applicable to a system, an engine, or a portion thereof.

It will be understood that when a unit, engine or module is referred to as being "on," "connected to," or "coupled to," another unit, engine, or module, it may be directly on, connected or coupled to, or communicate with the other unit, engine, or module, or an intervening unit, engine, or module may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of the present disclosure. It is to be expressly understood, however, that the drawings are for the purpose of illustration and description only and are not intended to limit the scope of the present disclosure. It is understood that the drawings are not to scale.

The flowcharts used in the present disclosure illustrate operations that systems implement according to some embodiments of the present disclosure. It is to be expressly understood, the operations of the flowcharts may be implemented not in order. Conversely, the operations may be implemented in inverted order, or simultaneously. Moreover, one or more other operations may be added to the flowcharts. One or more operations may be removed from the flowcharts.

In the present disclosure, an image of an object (e.g., a tissue, an organ, a tumor, a body, or the like) or a portion thereof (e.g., a part corresponding to a region of interest in the image) may be referred to as an "image," a "partial image," or the object itself. For example, an image of a lung may be referred to as a lung image or lung for brevity, and a region of interest corresponding to the lung image may be described as "the region of interest may include a lung." In some embodiments, an image may include a two-dimensional (2D) image and/or a three-dimensional (3D) image. The tiniest distinguishable element in an image may be termed as a pixel (in the 2D image) or a voxel (in the 3D image). Each pixel or voxel may represent a corresponding point of the object. For simplicity, the corresponding point of the object may be described as "the pixel" or "the voxel." For example, the projection data of a corresponding point of the object may be described as "the projection data of the voxel."

Some embodiments of the present disclosure relate to systems and methods for image generation. With the systems and the methods disclosed in the present disclosure, at least two original images may be generated based on same projection data according to different algorithms and processed and/or combined to generate a final image. A first original image may be better than a second original image in terms of a first feature, while the second original image is better than the first original image in terms of a second feature. The first feature or the second feature may relate to, e.g., artifact, CT number uniformity, etc. The final image may combine the merits of the at least two original images. The combination may lead to reduced artifacts and improved CT number uniformity in the final image. The first feature or the second feature may be obtained by applying a weighting function to the same projection data of the at least two original images. A weighting factor of the weighting function assigned to projection data of a voxel (e.g., a voxel of the first original image or the second original image) corresponding to a projection angle may be a normalized value of a first value of the weighting function and a second value of the weighting function. The normalization may for example, provide a good CT number uniformity for the first original image or the second original image. The systems and the methods may also achieve a high efficiency by reconstructing the at least two original images in parallel with a parallel hardware architecture. The parallel hardware architecture may obtain the same projection data and then reconstruct the at least two original images based on the same projection data respectively, in parallel, thereby reducing the number of times that the parallel hardware architecture reads the same projection data from, for example, a storage device.

Figure 1:
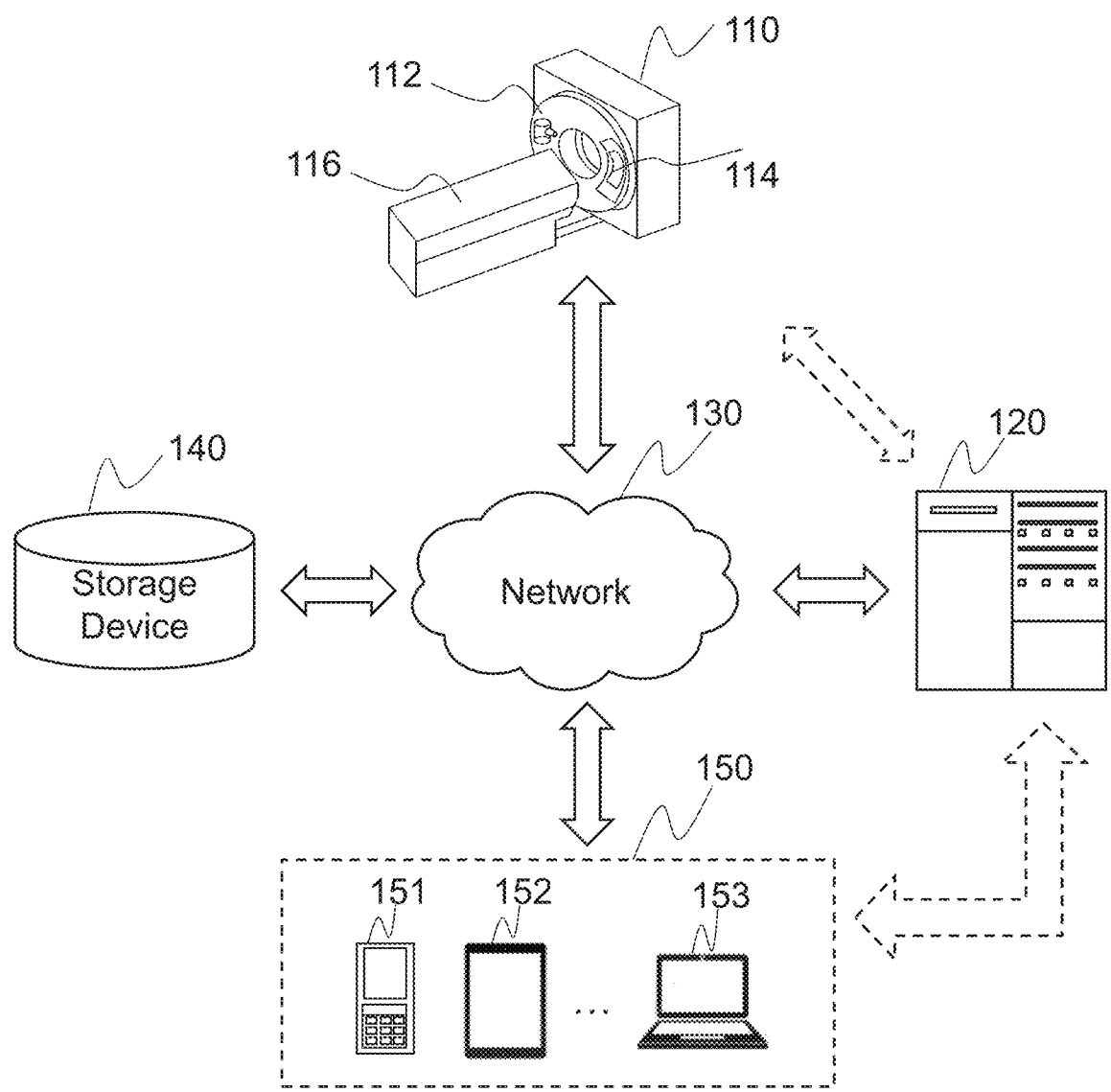
FIG. 1 is a schematic diagram illustrating an exemplary imaging system according to some embodiments of the present disclosure.

FIG. 1 is a schematic diagram illustrating an exemplary imaging system 100 according to some embodiments of the present disclosure. As shown, the imaging system 100 may include a scanner 110, a processing device 120, a network 130, a storage device 140, and one or more terminal devices 150. In some embodiments, the scanner 110, the processing device 120, the storage device 140, and/or the terminal device(s) 150 may be connected to and/or communicate with each other via a wireless connection (e.g., the network 130), a wired connection, or a combination thereof. The connection between the components in the imaging system 100 may be variable. Merely by way of example, the scanner 110 may be connected to the processing device 120 through the network 130, as illustrated in FIG. 1. As another example, the scanner 110 may be connected to the processing device 120 directly. As a further example, the storage device 140 may be connected to the processing device 120 through the network 130, as illustrated in FIG. 1, or connected to the processing device 120 directly.

The scanner 110 may generate or provide image data (e.g., projection data) via scanning an object, or a part of the object. The scanner 110 may include a single-modality scanner and/or a multi-modality scanner. The single-modality scanner may include, for example, a CT scanner, a magnetic resonance imaging (MRI) scanner, a positron emission tomography (PET) scanner, a single photon emission computed tomography (SPECT) scanner, a digital subtraction angiography (DSA) scanner, etc. In some embodiments, the CT scanner may include a cone beam CT (CBCT) scanner. The multi-modality scanner may include a SPECT-CT scanner, a PET-CT scanner, a SPECT-PET scanner, a DSA-MRI scanner, or the like, or any combination thereof. In some embodiments, the object being scanned may include a portion of a body, a substance, or the like, or any combination thereof. For example, the object may include a specific portion of a body, such as a head, a thorax, an abdomen, or the like, or any combination thereof. As another example, the object may include a specific organ, such as an esophagus, a trachea, a bronchus, a stomach, a gallbladder, a small intestine, a colon, a bladder, a ureter, a uterus, a fallopian tube, etc.

In some embodiments, the scanner 110 may transmit the image data via the network 130 to the processing device 120, the storage device 140, and/or the terminal device(s) 150. For example, the image data may be sent to the processing device 120 for further processing, or may be stored in the storage device 140.

For illustration purposes, the scanner 110 may be described as a CT scanner. It shall be noted that, in different situations, other types of scanners as described above may be used to perform the similar functions (e.g., acquiring image data) as the CT scanner. As shown in FIG. 1, the scanner 110 may include a radiation source 112, a detector 114, and a table 116. The radiation source 112 may scan an object or a portion thereof (e.g., the head, a breast, etc., of a patient) located on the table 116. The radiation source 112 may be configured to generate and/or deliver one or more radiation beams to the object. Exemplary radiation beams may include a particle beam, a photon beam, or the like, or any combination thereof. A particle beam may include a stream of neutrons, protons, electrons, heavy ions, or the like, or any combination thereof. A photon beam may include an X-ray beam, a γ-ray beam, a β-ray beam, an ultraviolet beam, a laser beam, or the like, or any combination thereof. The radiation beam may have the shape of a line, a narrow pencil, a narrow fan, a fan, a cone, a wedge, a tetrahedron, or the like, or any combination thereof. In some embodiments, the radiation source 112 may be a CBCT radiation source and the radiation beam may be a cone beam.

The detector 114 may detect one or more radiation beams emitted from the radiation source 112 or scattered by the object to generate image data (e.g., projection data). The image data may be transmitted to the processing device 120 for further processing. For example, the processing device 120 may reconstruct an image of the object or a portion thereof based on the image data.

In some embodiments, the detector 114 may include one or more detector units. A detector unit may include a scintillator detector (e.g., a cesium iodide detector, a gadolinium oxysulfide detector), a gas detector, etc. In some embodiments, the detector units may be arranged in a single row, two rows, or any other number of rows. Merely by way of example, the detector 114 may be a CT detector configured to detect X-rays.

The processing device 120 may process data and/or information obtained from the scanner 110, the storage device 140, and/or the terminal device(s) 150. For example, the processing device 120 may reconstruct one or more images based on the projection data collected by the scanner 110. In some embodiments, the processing device 120 may reconstruct more than one (e.g., two, three) images based on a same set of projection data that is acquired by the scanner 110 by scanning a same object. In some embodiments, the more than one images associated with the same set of projection data may be reconstructed by a processor having a parallel hardware architecture. The hardware architecture may perform operations (e.g., calculating the back-projection (BP) values of voxels in different images) in a parallel manner. In some embodiments, the processing device 120 may further process the reconstructed images by, for example, image filtering, eliminating saltation or noises in an image, image combination, or the like, or any combination thereof.

In some embodiments, the processing device 120 may be a single server, or a server group. The server group may be centralized, or distributed. In some embodiments, the processing device 120 may be local or remote. For example, the processing device 120 may access information and/or data stored in the scanner 110, the storage device 140, and/or the terminal device(s) 150 via the network 130. As another example, the processing device 120 may be directly connected to the scanner 110, the storage device 140, and/or the terminal device(s) 150 to access stored information and/or data. As a further example, the processing device 120 may be integrated in the scanner 110. In some embodiments, the processing device 120 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 120 may be implemented in a computing device 200 having one or more components illustrated in FIG. 2 in the present disclosure.

The network 130 may include any suitable network that can facilitate the exchange of information and/or data for the imaging system 100. In some embodiments, one or more components of the imaging system 100 (e.g., the scanner 110, the processing device 120, the storage device 140, and/or the terminal device 150(s)) may communicate information and/or data with one or more other components of the imaging system 100 via the network 130. For example, the processing device 120 may obtain image data from the scanner 110 via the network 130. As another example, the processing device 120 may obtain user instructions from the terminal device(s) 150 via the network 130. The network 130 may include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, witches, server computers, or the like, or any combination thereof. For example, the network 130 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 130 may include one or more network access points. For example, the network 130 may include wired and/or wireless network access points such as base stations and/or internet exchange points through which one or more components of the imaging system 100 may be connected to the network 130 to exchange data and/or information.

The storage device 140 may store data, instructions, and/or any other information. In some embodiments, the storage device 140 may store data obtained from the scanner 110, the processing device 120 and/or the terminal device(s) 150. In some embodiments, the storage device 140 may store data and/or instructions that the processing device 120 may execute or use to perform exemplary methods described in the present disclosure. For example, the storage device 140 may store projection data obtained from the scanner 110. The processing device 120 may further access the projection data and reconstruct one or more images based on the projection data.

In some embodiments, the storage device 140 may include mass storage, removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), a digital versatile disk ROM, etc. In some embodiments, the storage device 140 may be implemented on a cloud platform as described elsewhere in the disclosure.

In some embodiments, the storage device 140 may be connected to the network 130 to communicate with one or more other components in the imaging system 100 (e.g., the scanner 110, the processing device 120 or the terminal device(s) 150). One or more components in the imaging system 100 may access the data or instructions stored in the storage device 140 via the network 130. In some embodiments, the storage device 140 may be directly connected to or communicate with one or more components of the imaging system 100 (e.g., the processing device 120, the terminal device(s) 150). In some embodiments, the storage device 140 may be part of the processing device 120.

The terminal device(s) 150 may be connected to and/or communicate with the scanner 110, the processing device 120, the network 130, and/or the storage device 140. In some embodiments, the scanner 110 may be operated from the terminal device(s) 150 via, e.g., a wireless connection. In some embodiments, the terminal device(s) 150 may receive information and/or instructions inputted by a user, and send the received information and/or instructions to the scanner 110 or to the processing device 120 via the network 130. In some embodiments, the terminal device(s) 150 may receive data and/or information from the processing device 120 and/or the scanner 110. For example, the terminal device(s) 150 may receive a processed image from the processing device 120. As another example, the terminal device(s) 150 may obtain image data acquired via the scanner 110 and transmit the image data to the processing device 120. In some embodiments, the terminal device(s) 150 may be part of or communicate with the processing device 120. In some embodiments, the terminal device(s) 150 may be omitted.

In some embodiments, the terminal device(s) 150 may include a mobile device 151, a tablet computer 152, a laptop computer 153, or the like, or any combination thereof. The mobile device 151 may include a smart home device, a wearable device, a smart mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a smart bracelet, smart footgear, a pair of smart glasses, a smart helmet, a smart watch, smart clothing, a smart backpack, a smart accessory, or the like, or any combination thereof. In some embodiments, the smart mobile device may include a smartphone, a personal digital assistant (PDA), a gaming device, a navigation device, a point of sale (POS) device, or the like, or any combination thereof. In some embodiments, the virtual reality device and/or the augmented reality device may include a virtual reality helmet, a virtual reality glass, a virtual reality patch, an augmented reality helmet, an augmented reality glass, an augmented reality patch, or the like, or any combination thereof. For example, the virtual reality device and/or the augmented reality device may include a Google Glass™, an Oculus Rift™, a Hololens™, a Gear VR™, etc.

This description is intended to be illustrative, and not to limit the scope of the present disclosure. Many alternatives, modifications, and variations will be apparent to those skilled in the art. The features, structures, methods, and characteristics of the exemplary embodiments described herein may be combined in various ways to obtain additional and/or alternative exemplary embodiments. For example, the storage device 140 may be a data storage including cloud computing platforms, such as, public clouds, private clouds, community clouds, hybrid clouds, etc. In some embodiments, the processing device 120 may be integrated into the scanner 110. However, those variations and modifications do not depart the scope of the present disclosure.

FIG. 2 is a schematic diagram illustrating exemplary hardware and/or software components of an exemplary computing device 200 on which the processing device 120 may be implemented according to some embodiments of the present disclosure. As illustrated in FIG. 2, the computing device 200 may include a processor 210, a storage 220, an input/output (I/O) 230, and a communication port 240.

The processor 210 may execute computer instructions (program code) and perform functions of the processing device 120 in accordance with techniques described herein. The computer instructions may include, for example, routines, programs, objects, components, signals, data structures, procedures, modules, and functions, which perform particular functions described herein. In some embodiments, the processor 210 may process data obtained from the scanner 110, the storage device 140, the terminal device(s) 150, and/or any other component of the imaging system 100. For example, the processor 210 may reconstruct one or more images based on projection data obtained from the scanner 110. In some embodiments, the reconstructed image may be stored in the storage device 140, the storage 220, etc. In some embodiments, the reconstructed image may be displayed on a display device by the I/O 230. In some embodiments, the processor 210 may perform instructions obtained from the terminal device(s) 150. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combination thereof.

Merely for illustration, only one processor is described in the computing device 200. However, it should be noted that the computing device 200 in the present disclosure may also include multiple processors, thus operations and/or method steps that are performed by one processor as described in the present disclosure may also be jointly or separately performed by the multiple processors. For example, if in the present disclosure the processor of the computing device 200 executes both process A and process B, it should be understood that process A and process B may also be performed by two or more different processors jointly or separately in the computing device 200 (e.g., a first processor executes process A and a second processor executes process B, or the first and second processors jointly execute processes A and B).

The storage 220 may store data/information obtained from the scanner 110, the storage device 140, the terminal device(s) 150, or any other component of the imaging system 100. In some embodiments, the storage 220 may include a mass storage device, a removable storage device, a volatile read-and-write memory, a read-only memory (ROM), or the like, or any combination thereof. For example, the mass storage may include a magnetic disk, an optical disk, a solid-state drive, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage 220 may store one or more programs and/or instructions to perform exemplary methods described in the present disclosure. For example, the storage 220 may store a program or algorithm, when executed by the processing device 120, may reduce artifacts in an image. In some embodiments, the storage 220 may store one or more intermediate results generated during an image reconstruction process. For example, the storage 220 may store one or more BP values calculated according to the projection data. The stored BP values may be further retrieved by the processor 210 or any other processing component in the image system 110 for further processing (e.g., image reconstruction).

The I/O 230 may input or output signals, data, and/or information. In some embodiments, the I/O 230 may enable a user interaction with the processing device 120. In some embodiments, the I/O 230 may include an input device and an output device. Exemplary input devices may include a keyboard, a mouse, a touch screen, a microphone, or the like, or any combination thereof. Exemplary output devices may include a display device, a loudspeaker, a printer, a projector, or the like, or any combination thereof. Exemplary display devices may include a liquid crystal display (LCD), a light-emitting diode (LED)-based display, a flat panel display, a curved screen, a television device, a cathode ray tube (CRT), or the like, or any combination thereof.

The communication port 240 may be connected to a network (e.g., the network 130) to facilitate data communications. The communication port 240 may establish connections between the processing device 120 and the scanner 110, the storage device 140, or the terminal device(s) 150. The connection may be a wired connection, a wireless connection, or combination of both that enables data transmission and reception. The wired connection may include an electrical cable, an optical cable, a telephone wire, or the like, or any combination thereof. The wireless connection may include Bluetooth™, Wi-Fi, WiMax, WLAN, Zig-Bee™, mobile network (e.g., 3G, 4G, 5G, etc.), or the like, or any combination thereof. In some embodiments, the communication port 240 may be a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
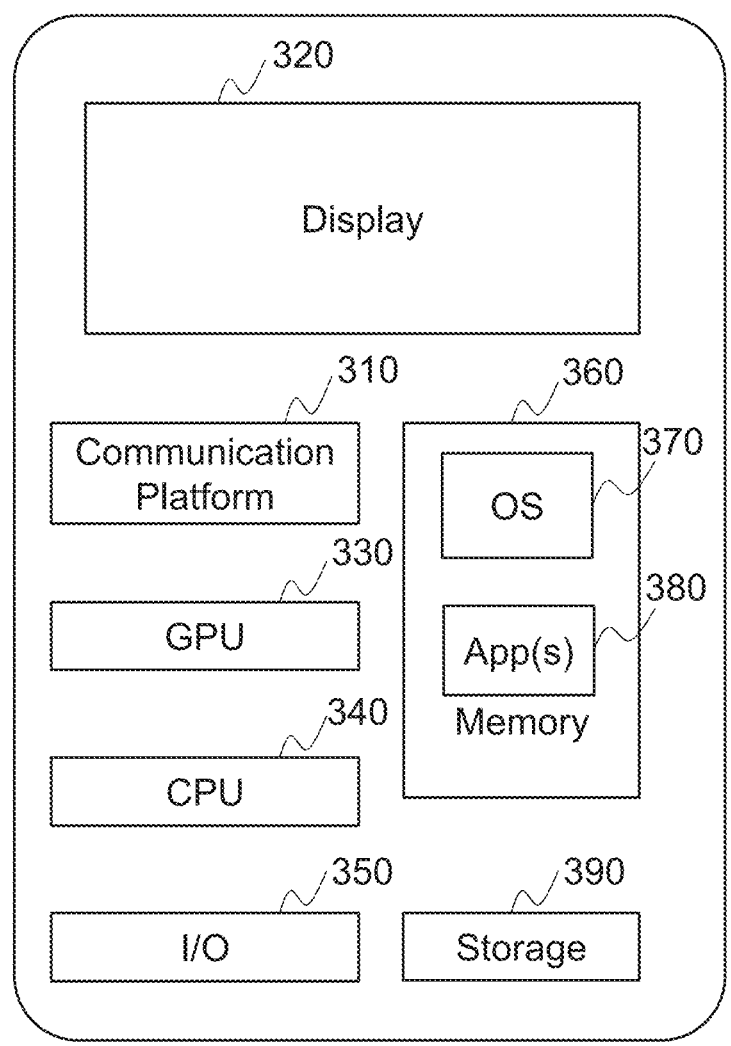
FIG. 3 is a schematic diagram illustrating exemplary hardware and/or software components of a mobile device according to some embodiments of the present disclosure.

FIG. 3 a schematic diagram illustrating exemplary hardware and/or software components of an exemplary mobile device 300 according to some embodiments of the present disclosure. In some embodiments, the processing device 120 and/or the terminal device(s) 150 may be implemented on the mobile device 300 via its hardware, software program, firmware, or any combination thereof. As illustrated in FIG. 3, the mobile device 300 may include a communication platform 310, a display 320, a graphic processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS™, Android™, Windows Phone™, etc.) and one or more applications 380 may be loaded into the memory 360 from the storage 390 in order to be executed by the CPU 340. The applications 380 may include a browser or any other suitable mobile apps for receiving and rendering information relating to image processing or other information from the processing device 120. User interactions with the information stream may be achieved via the I/O 350 and provided to the processing device 120 and/or other components of the imaging system 100 via the network 120.

To implement various modules, units, and their functionalities described in the present disclosure, computer hardware platforms may be used as the hardware platform(s) for one or more of the elements described herein. A computer with user interface elements may be used to implement a personal computer (PC) or other type of work station or terminal device, although a computer may also act as a server if appropriately programmed. It is believed that those skilled in the art are familiar with the structure, programming and general operation of such computer equipment and as a result the drawings should be self-explanatory.

Figure 4:
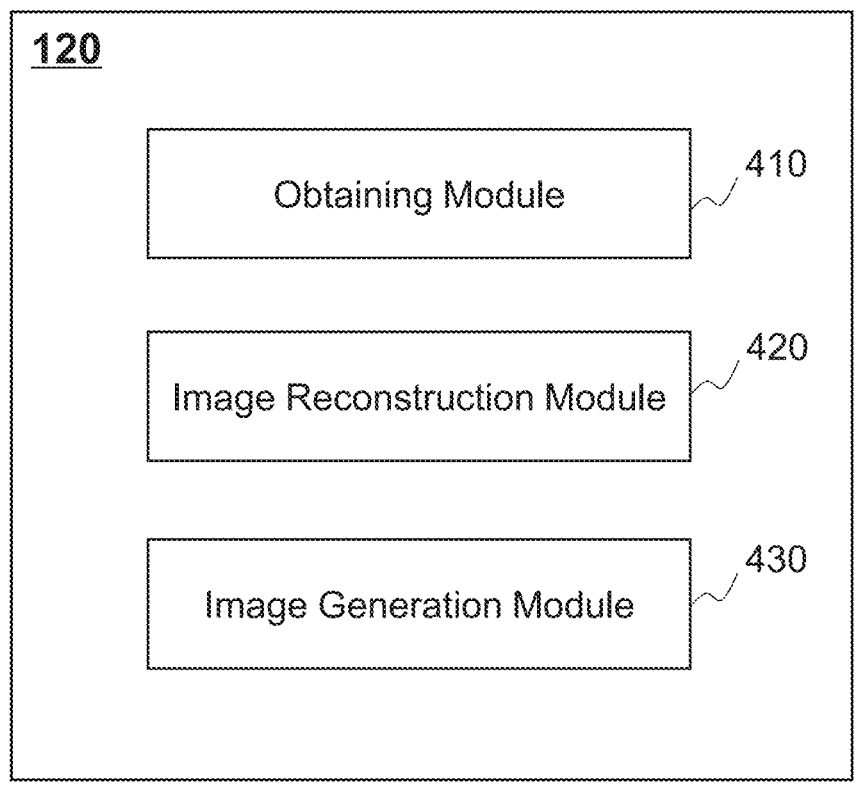
FIG. 4 is a block diagram illustrating an exemplary processing device according to some embodiments of the present disclosure.

FIG. 4 is block diagram illustrating an exemplary processing device 120 according to some embodiments of the present disclosure. The processing device 120 may include an obtaining module 410, an image reconstruction module 420, and an image generation module 430. At least a portion of the processing device 120 may be implemented on a computing device as illustrated in FIG. 2 or a mobile device as illustrated in FIG. 3.

The obtaining module 410 may obtain projection data. In some embodiments, the obtaining module 410 may obtain the projection data from the scanner 110, the storage device 140, the terminal device(s) 150, and/or an external data source (not shown). In some embodiments, the projection data may be generated based on detected radiation beams (e.g., X-ray beams) at least some of which have passed through an object being radiated in the scanner 110. The object may include substance, tissue, an organ, a specimen, a body, or the like, or any combination thereof. In some embodiments, the object may include a head, a breast, a lung, a pleura, a mediastinum, an abdomen, a long intestine, a small intestine, a bladder, a gallbladder, a triple warmer, a pelvic cavity, a backbone, extremities, a skeleton, a blood vessel, or the like, or any combination thereof. In some embodiments, the projection data may be transmitted to the image reconstruction module 420 for further processing. The image reconstruction module 420 may reconstruct at least one image of the object or a portion thereof based on the projection data. In some embodiments, the projection data may be transmitted to a storage module of the processing device 120 to be stored.

The image reconstruction module 420 may reconstruct one or more images based on projection data (e.g., the projection data obtained from the obtaining module 410, the storage module of the processing device 120, and/or the storage device 140). In some embodiments, the image reconstruction module 420 may reconstruct an image according to a reconstruction technique including, for example, an iterative reconstruction algorithm (e.g., a statistical reconstruction algorithm), a Fourier slice theorem algorithm, a filtered back projection (FBP) algorithm, a fan-beam reconstruction algorithm, an analytic reconstruction algorithm, or the like, or any combination thereof. In some embodiments, the image reconstruction module 420 may reconstruct more than one (e.g., two, three) images based on a same set of projection data of an object according to a weighting function. The image reconstruction module 420 may apply the weighting function to the same set of projection data of the object to obtain weighted projection data, and back-project the weighted projection data to generate an image of the object. In some embodiments, weighting functions associated with the more than one images may be different. In some embodiments, the more than one images associated with the same set of projection data may be reconstructed by a processor having a parallel hardware architecture. The parallel hardware architecture may perform operations (e.g., calculating the BP values of voxels in different images) in a parallel manner. More descriptions of the weighting function and/or the reconstruction of an image may be found elsewhere in the disclosure (e.g., FIG. 7 and/or FIG. 9 and the descriptions thereof). In some embodiments, the image reconstruction module 420 may perform pre-processing operations on the projection data before the reconstruction. Exemplary pre-processing operation may include, projection data normalization, projection data smoothing, projection data suppressing, projection data encoding (or decoding), preliminary denoising, etc.

The image generation module 430 may generate a final image based on at least two original images. In some embodiments, the image generation module 430 may obtain the at least one two original images from the image reconstruction module 420, a storage module of the processing device 120, the storage device 140, or the terminal device(s) 150. The image generation module 430 may generate the final image based on one or more operations including, for example, an image subtraction operation, a masking operation, a data extraction operation, a low-pass filtering operation, an image combination operation, etc. A first original image may be better than a second original image in terms of a first feature (e.g., a feature relating to artifact), while the second original image is better than the first original image in terms of a second feature (e.g., a feature relating to CT number uniformity). The final image may combine the merits of the at least two original images. For example, the final image may present reduced artifacts and improved CT number uniformity. More descriptions of the generation of the final image may be found elsewhere in the disclosure (e.g., FIG. 8 and the description thereof).

Figure 5:
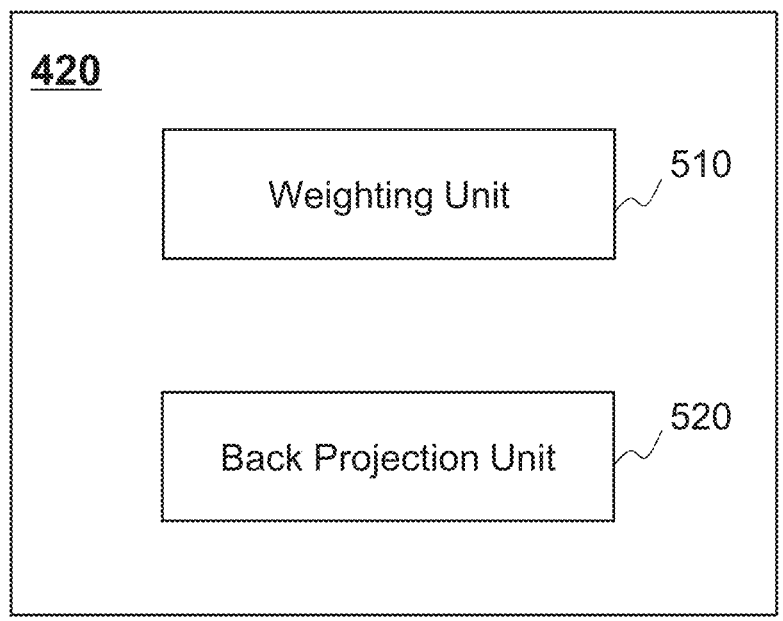
FIG. 5 is a block diagram illustrating an exemplary image reconstruction module according to some embodiments of the present disclosure.

In some embodiments, one or more modules illustrated in FIG. 5 may be implemented in at least part of the imaging system 100 as illustrated in FIG. 1. For example, the obtaining module 410, the image reconstruction module 420, and/or the image generation module 430 may be integrated into a console (not shown). Via the console, a user may set parameters for scanning an object, controlling the imaging processes, adjusting parameters for reconstructing an image, etc. In some embodiments, the console may be implemented via the processing device 120 and/or the terminal device(s) 150.

FIG. 5 is a block diagram illustrating an exemplary image reconstruction module 420 according to some embodiments of the present disclosure. The image reconstruction module 420 may include a weighting unit 510 and a back projection unit 520. At least a portion of the image reconstruction module 420 may be implemented on a computing device as illustrated in FIG. 2 or a mobile device as illustrated in FIG. 3.

The weighting unit 510 may perform a weighting operation on projection data. For example, the weighting unit 510 may assign a weighting factor to projection data of a voxel to obtain weighted projection data of the voxel. In some embodiments, the weighting factor may be determined according to a weighting function. More descriptions of the weighting operation may be found elsewhere in the disclosure (e.g., FIG. 9 and the description thereof). In some embodiments, the weighted projection data may be transmitted to the back projection unit 520 for back-projecting the weighted projection data.

The back projection unit 520 may back-project projection data of a voxel. For example, the back projection unit 520 may back-project the weighted projection data of the voxel obtained from the weighting unit 510 to obtain back-projected data of the voxel. In some embodiments, the back projection unit 520 may perform the back-projection operation by transforming the projection data from a projection domain to an image domain.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, the weighting unit 510 and the back projection unit 520 may be integrated into an independent unit. As another example, the image reconstruction module 420 may include a storage unit.

Figure 6:
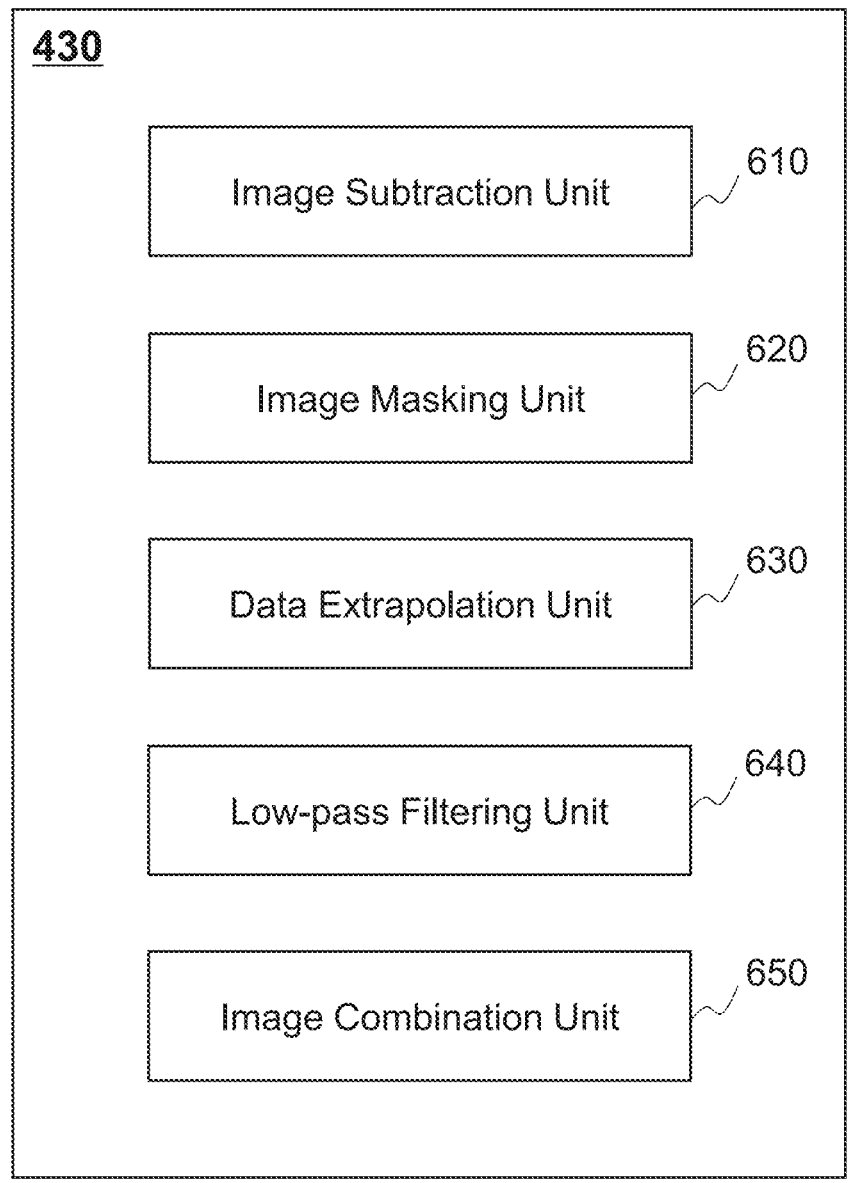
FIG. 6 is a block diagram illustrating an exemplary image generation module according to some embodiments of the present disclosure.

FIG. 6 is a block diagram illustrating an exemplary image generation module 430 according to some embodiments of the present disclosure. The image generation module 430 may include an image subtraction unit 610, an image masking unit 620, a data extrapolation unit 630, a low-pass filtering unit 640, and an image combination unit 650. At least a portion of the image generation module 430 may be implemented on a computing device as illustrated in FIG. 2 or a mobile device as illustrated in FIG. 3.

The image subtraction unit 610 may generate a difference image based on a first image and a second image by, e.g., subtraction. In some embodiments, the image subtraction unit 610 may obtain the first image and/or the second image from the image reconstruction module 420, the storage device 140, a storage module of the processing device 120, or an external storage device. In some embodiments, the image subtraction unit 610 may generate the difference image by subtracting one image from the other. For example, the image subtraction unit 610 may generate the difference image by subtracting the first image from the second image. As another example, the image subtraction unit 610 may generate the difference image by subtracting the second image from the first image. More descriptions of the subtraction may be found elsewhere in the disclosure (e.g., FIG. 8 and the description thereof). In some embodiments, the difference image may be transmitted to the image masking unit 620 for performing a masking operation on the difference image. In some embodiments, the first image may be transmitted to the image combination unit 650 for combining the first image with another image.

The image masking unit 620 may perform a masking operation on an image. For example, the image masking unit 620 may generate a fourth image by performing a masking operation on the difference image obtained from the image subtraction unit 610. In some embodiments, the masking operation may include applying a mask (e.g., a two-dimensional matrix, a three-dimensional matrix) on the difference image. By applying the mask on the difference image (e.g., making the mask multiply by the difference image), the image masking unit 620 may reset the values of the pixels/voxels (e.g., gray values) in a region of the difference image to a default value (e.g., "0" for gray value), and the values of the pixels/voxels (e.g., gray values) in another region of the difference image may remain unchanged. More descriptions of the making operation may be found elsewhere in the disclosure (e.g., FIG. 8 and the description thereof). In some embodiments, the fourth image may be transmitted to the data extrapolation unit 630 for performing a data extrapolation operation on the fourth image.

The data extrapolation unit 630 may perform a data extrapolation operation on an image. For example, the data extrapolation unit 630 may generate a fifth image by performing a data extrapolation operation on the fourth image obtained from the image masking unit 620. A data extrapolation operation may be a process in which the value of a specific data point is estimated based on the values of data points in the vicinity of the specific data point in space. By performing the data extrapolation operation on the fourth image, the data extrapolation unit 630 may assign the values of a pixel/voxel (e.g., gray value) in a region of the fourth image based on the values of pixels/voxels (e.g., gray values) in another region of the fourth image. More descriptions of the data extrapolation operation may be found elsewhere in the disclosure (e.g., FIG. 8 and the description thereof). In some embodiments, the fifth image may be transmitted to the low-pass filtering unit 640 for performing a low-filtering operation on the fifth image.

The low-pass filtering unit 640 may perform a low-pass filtering operation on an image. For example, the low-pass filtering unit 640 may generate a sixth image by performing a low-pass filtering operation on the fifth image obtained from the data extrapolation unit 630. The low-pass filtering unit 640 may perform the low-pass filtering operation on the fifth image using a low-pass filter, such as, a Gaussian low-pass filter, a Butterworth low-pass filter, a Chebyshev low-pass filter, a 3D box filter (e.g., a 3×3×3 box filter), or the like, or any combination thereof. More descriptions of the low-pass filtering operation may be found elsewhere in the disclosure (e.g., FIG. 8 and the description thereof). In some embodiments, the sixth image may be transmitted to the image combination unit 650 for combining the sixth image with another image.

The image combination unit 650 may combine at least two images. For example, the image combination unit 650 may combine the sixth image obtained from the low-pass filtering unit 640 and the first image obtained from the image reconstruction module 420. The image combination may refer to a combination of data (e.g., gray value) of corresponding pixels/voxels in the sixth image and the first image. During the image combination, the image generation module 430 may apply one or more of various operations including, for example, an addition operation, a subtraction operation, a multiplication operation, a division operation, or any combination thereof.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, the image generation module 430 may include a storage unit for storing images obtained from the image subtraction unit 610, the image masking unit 620, the data extrapolation unit 630, the low-pass filtering unit 640, and/or the image combination unit 650.

Figure 7:
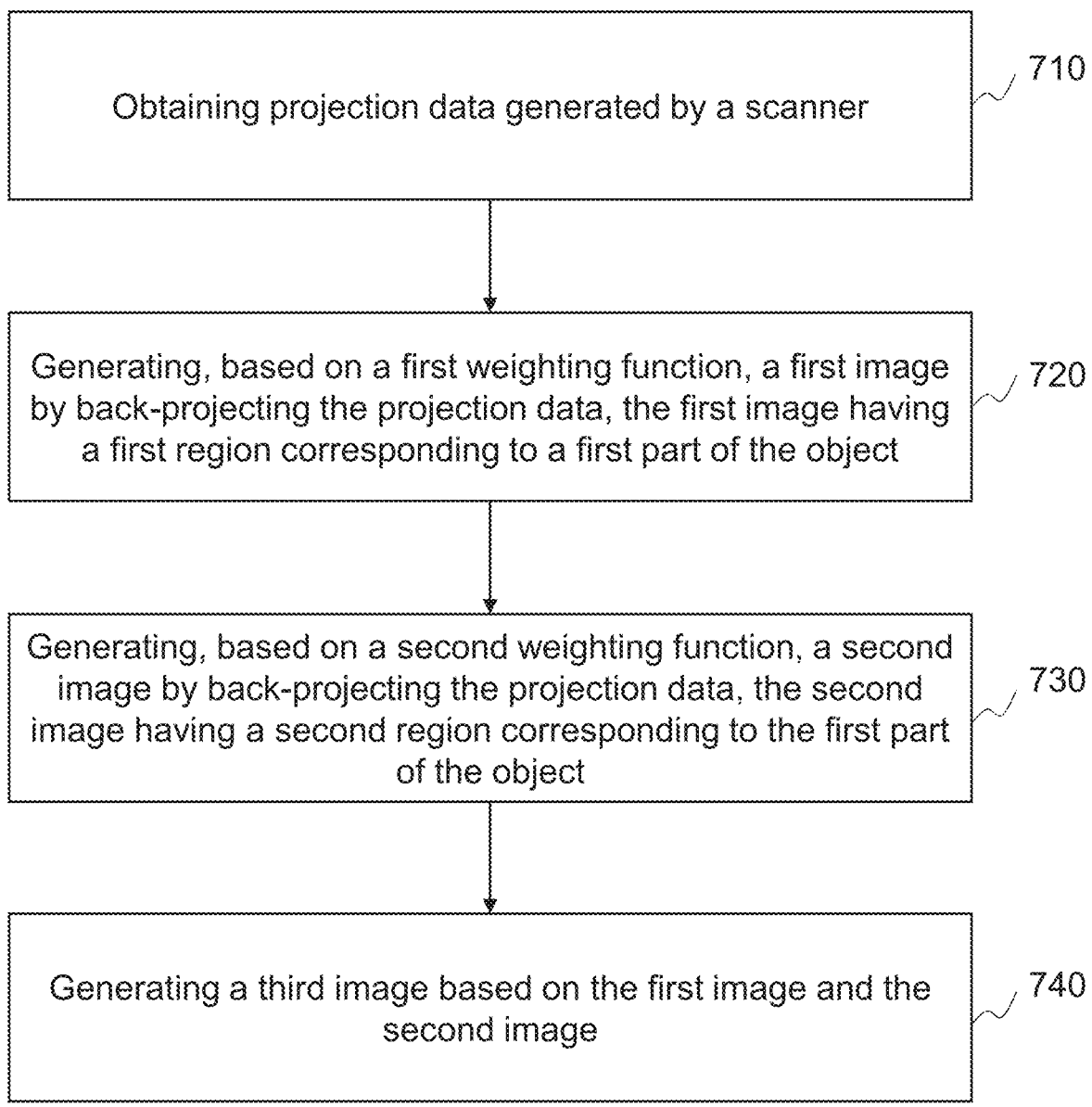
FIG. 7 is a flowchart illustrating an exemplary process for generating an image according to some embodiments of the present disclosure.

FIG. 7 is a flowchart illustrating an exemplary process 700 for generating an image according to some embodiments of the present disclosure. The process 700 may be executed by the imaging system 100. For example, the process 700 may be stored in the storage device 140 and/or the storage 220 in the form of instructions (e.g., an application), and invoked and/or executed by the processing device 120 (e.g., the processor 210 illustrated in FIG. 2, or one or more modules in the processing device 120 illustrated in FIG. 4). The operations of the illustrated process presented below are intended to be illustrative. In some embodiments, the process 700 may be accomplished with one or more additional operations not described, and/or without one or more of the operations discussed. Additionally, the order in which the operations of the process 700 as illustrated in FIG. 7 and described below is not intended to be limiting.

In 710, the processing device 120 (e.g., the obtaining module 410) may obtain projection data generated by a scanner. For example, the processing device 120 may obtain the projection data from the scanner 110 via, for example, the network 130. The scanner may acquire the projection data by scanning an object (e.g., a head, a breast). For example, a radiation source of the scanner (e.g., the radiation source 112 of the scanner 110) may emit radiation beams (e.g., X-ray beams) to the object. A detector of the scanner (e.g., the detector 114 of the scanner 110) may acquire the projection data based on detected radiation beams, at least some of which may have passed through the object.

Figure 11:
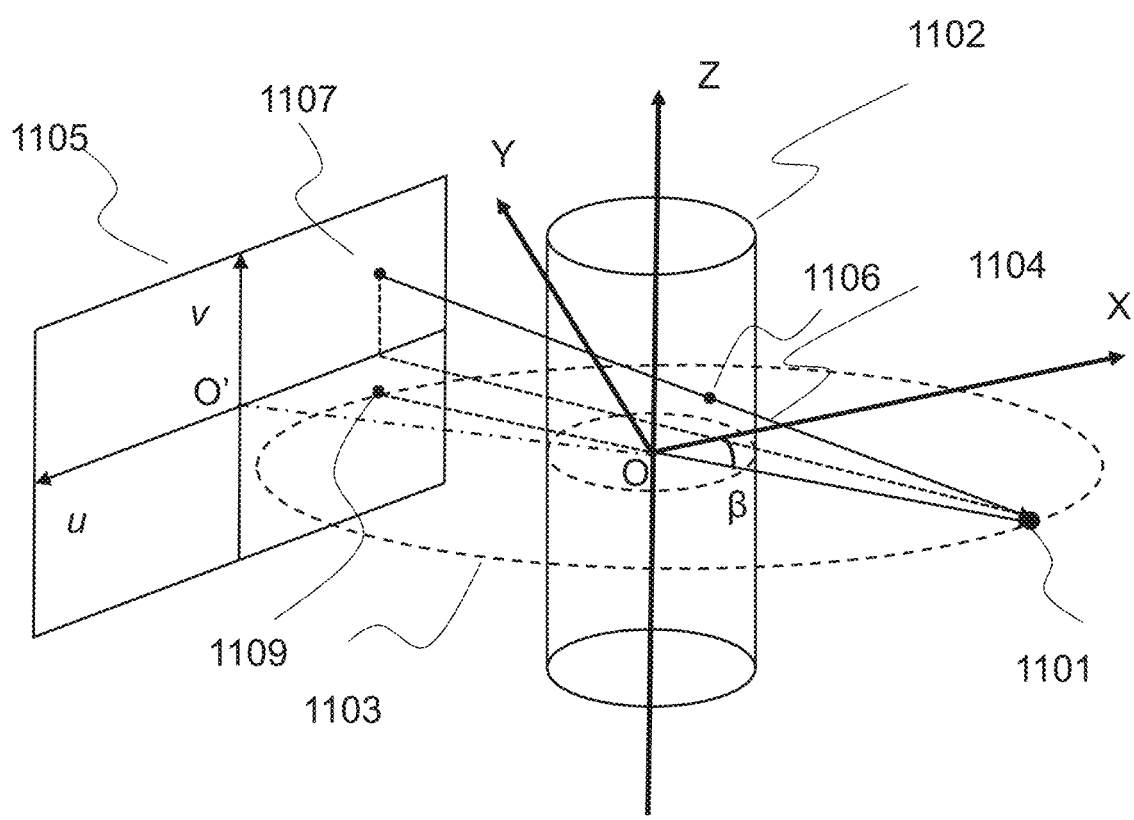
FIG. 11 is a schematic diagram illustrating an exemplary coordinate system for the scanning of an object according to some embodiments of the present disclosure.

In some embodiments, the radiation source may scan the object by emitting radiation beams toward the object from different projection angles to produce the projection data. The different projection angles may fall within an angle range. For example, the radiation source may scan the object along a circular trajectory covering an angle range of 360°. As another example, the radiation source may scan the object along a trajectory covering an angle range less than 360° (e.g., 90°, 180°, 240°). As used herein, a projection angle is the angle between the line connecting the radiation source and the origin of a coordinate system and an axis of the coordinate system, e.g., the positive X axis of the coordinate system. See, for example, FIG. 11 providing a schematic diagram of an exemplary coordinate system for the scanning of an object. As shown in FIG. 11, the radiation source of a scanner may scan an object 1102 along a circular trajectory 1103. The scanner may be a CBCT scanner and the radiation source may emit cone beams to the object 1102. The isocenter O of the scanner may coincide with the origin of the coordinate system that is an XYZ coordinate system as illustrated. When the radiation source is located at the position 1101, it may correspond to a projection angle β, which is the angle between the line connecting the radiation source and the origin O (i.e., line O O') and the positive X axis of the XYZ coordinate system.

In 720, the processing device 120 (e.g., the image reconstruction module 420) may generate, based on a first weighting function, a first image by back-projecting the projection data. In some embodiments, the first image may be a 2D image, a 3D image, a four-dimensional (4D) image, etc.

The first image may have different regions corresponding to different parts of the object. For example, the first image may have a specific region corresponding to a specific part of the object. In some embodiments, due to the shape of the radiation beams emitted from the radiation source, the specific part of the object may not be radiated by the radiation source from a specific projection angle.

Figure 10:
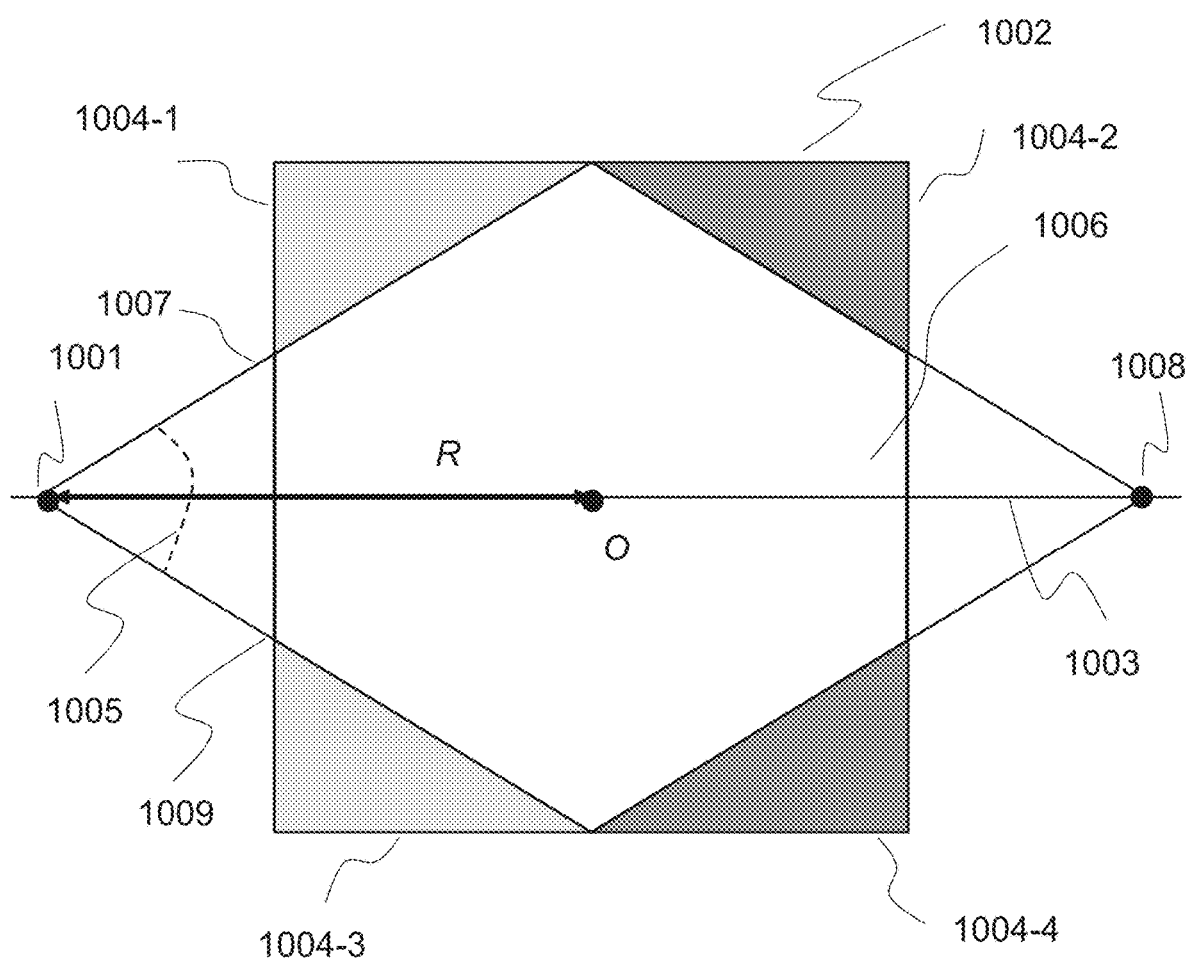
FIG. 10 is a schematic diagram illustrating an exemplary scanning region according to some embodiments of the present disclosure.

For example, FIG. 10 illustrates an exemplary scanning region according to some embodiments of the present disclosure. As illustrated in FIG. 10, a scanning region 1002 may show a cross section of an object that is scanned by a radiation source of a scanner moving along a circular trajectory. The rotation center of the circular trajectory may be the isocenter of the scanner, which is denoted by O in FIG. 10. The circular trajectory passes through positions 1001 and 1008, and is located in a plane 1003 perpendicular to the scanning region 1002. The scanner may be a CBCT scanner whose radiation source emits cone beams. R may denote the distance between the radiation source at the position 1001 and the isocenter O.

The scanning region 1002 may include four corner regions 1004-1, 1004-2, 1004-3, and 1004-4, and a center region 1006. Each of the four corner regions 1004-1, 1004-2, 1004-3, and 1004-4 is represented by a triangular shape in a plane (e.g., a cross section of the object) of the scanning region 1002 and may show a first part of the object located in a corner region of the image or scanning region 1002. The center region 1006 may show a second part of the object located in a center region of the scanning region 1002. For brevity, a part of the object located in a corner region of the scanning region 1002 in a scan may be referred to as a corner part of the object, and a part of the object located in a center region of the scanning region 1002 in a scan may be referred to as a center part of the object. For brevity, a corner region of the scanning region may correspond to a corner region of an image generated based on projection data acquired by scanning an object located in the scanning region. Similarly, a center region of the scanning region may correspond to a center region of an image generated based on projection data acquired by scanning an object located in the scanning region. For brevity, the object is assumed to be positioned in the scanning region such that a center part of the object is located in the center region of the scanning region and accordingly a center region of a generated image and that a corner part of the object is located in a corner region of the scanning region and accordingly a corner region of a generated image. When the radiation source is located at the position 1001, the lines 1007 and 1009 may delineate the boundary of the radiation beams that can be detected by the detector. The lines 1007 and 1009 may form a cone angle 1005 in the plane of the image 1002. The corner regions 1004-1 and 1004-3 are not radiated by the radiation source from the position 1001; in contrast, the corner regions 1004-2 and 1004-4 and the center region 1006 are radiated by the radiation source from the position 1001. Similarly, when the radiation source is located at the position 1008, the corner regions 1004-2 and 1004-4 are not radiated by the radiation source, and the corner regions 1004-1, 1004-3 and the center region 1006 are radiated by the detector. Therefore, the corner parts of the object may be radiated by the radiation source from angles in an angle range less than 360°, and the center part of the object may be radiated by the radiation source from angles in an angle range of 360°.

It shall be appreciated that the lack of radiation at specific projection angles may lead to insufficient projection data for a certain part of the object (e.g., a corner part), and cause one or more of various deficiencies, such as, artifacts, reduction of CT number uniformity, etc., in a reconstructed image of the object. To cure these and other deficiencies, the processing device 120 may apply a first weighting function to the projection data of the object to obtain first weighted projection data, and back-project the first weighted projection data to generate the first image of the object. When the processing device 120 applies the first weighting function to the projection data of the object, the projection data corresponding to a center part of the object (e.g., the projection data generated from radiation beams only passing through the center part of the object) may be assigned a weighting factor different from the projection data corresponding to a corner part of the object (e.g., the projection data generated from radiation beams passing through the corner part of the object). For example, as illustrated in FIG. 10, the projection data generated from the radiation beams that pass through the corner regions 1004-2 and 1004-4 may be assigned a lower weighting factor than that of the projection data generated from the radiation beams that only pass through the center region 1006 according to the first weighting function. In some embodiments, the first weighting function may be described as an aperture weighting function. The weighting factor applied to the projection data may be associated with the projection angle corresponding to the projection data. More descriptions of an aperture weighting function may be found elsewhere in the disclosure. See, e.g., FIG. 12 and the description thereof.

In 730, the processing device 120 (e.g., the image reconstruction module 420) may generate, based on a second weighting function, a second image by back-projecting the projection data. In some embodiments, the second image may be a 2D image, a 3D image, a 4D image, etc.

The second image may show the same part of the object as the first image. For example, the second image may also have a corner region (e.g., the corner region 1004-1, 1004-2, 1004-3, or 1004-4 illustrated in FIG. 10) corresponding to one of the corner parts of the object. The second image may also have a center region (e.g., the center region 1006 illustrated in FIG. 10) corresponding to the center part of the object. In some embodiments, the size of the first image may be same as the size of the second image. Alternatively or additionally, the voxel (or pixel) count of the first image may be same as that of the second image. In some embodiments, the size of the first image may be different from the size of the second image. At least a portion of the first image and at least a portion of the second image may correspond to a same portion of the object.

Similar to the generation of the first image as illustrated in 720, the processing device 120 may apply the second weighting function to the projection data to obtain second weighted projection data, and back-project the second weighted projection data to generate the second image of the object. When the processing device 120 applies the second weighting function to the projection data of the object, the projection data corresponding to a center part of the object (e.g., the projection data generated from radiation beams only passing through the center part of the object) may be assigned a weighting factor different from the projection data corresponding to a corner part of the object (e.g., the projection data generated from radiation beams passing through the corner part of the object).

The first weighting function and the second weighting function may affect the qualities (e.g., artifact, CT number uniformity) of the first image and the second image. In some embodiments, the first weighting function and the second weighting function may be derived from a same or different aperture weighting functions. For example, one or more parameters in a same aperture weighting function, when assigned different values, may produce the first weighting function and the second weighting function, respectively. Merely by way of example, the same aperture weighting function may include a first parameter and a second parameter. The values of the first parameter and the second parameter may affect the qualities of the first image and the second image. In some embodiments, the first weighting function and the second weighting function may be assigned the same value of the second parameter. Additionally, the first weighting function may be assigned a smaller value of the first parameter than the second weighting function. Accordingly, as described elsewhere in the disclosure, the first image may include fewer artifacts and better high frequency components than the second image. Further, a corner region of the first image may include better low frequency components than the corresponding corner region of the second image. Moreover, the second image may present a better CT number uniformity than the first image. The center region of the second image may include better low frequency components than the corresponding center region of the first image.

In some embodiments, the processing device 120 may obtain the first weighting function and/or the second weighting function from the storage device 140. The first weighting function and the second weighting function may be configured to emphasize and/or suppress different features of the projection data corresponding to different regions of the scanning region (and different parts of the object located in these different regions of the scanning region). For example, a plurality of weighting functions, including one or more aperture weighting functions, may be stored in the storage device 140 in the form of a lookup table, and thus the processing device 120 may retrieve the first weighting function and/or the second weighting function from the lookup table. More descriptions of an aperture weighting function may be found elsewhere in the disclosure. See, e.g., FIG. 12 and the description thereof.

In some embodiments, the processing device 120 may include a parallel hardware architecture having a plurality of processing threads that can execute two or more operations concurrently. For example, a processing thread "A" and a processing thread "B" may perform at least part of the operation 720 and at least part of the operation 730 concurrently. For illustration purposes, after the acquisition of the projection data corresponding to a voxel at a specific projection angle, the processing thread "A" and the processing thread "B" may determine the values of the voxel in the first and second images, respectively, in parallel. Specifically, the processing thread "A" may determine the weighting factor to be applied on the voxel according to the first weighting function, and concurrently, the processing thread "B" may determine the weighting factor to be applied on the voxel according to the second weighting function. Alternatively or additionally, the processing thread "A" may perform the weighting operation on the projection data with respect to the voxel in the first image according to the first weighting function, and concurrently, the processing thread "B" may perform the weighting operation on the projection data with respect to the voxel in the second image according to the second weighting function. Alternatively or additionally, the processing thread "A" may perform the back-projection operation on the weighted projection data with respect to the voxel in the first image, and concurrently, the processing thread "B" may perform the back-projection operation on the weighted projection data with respect to the voxel in the second image. In some embodiments, the parallel hardware architecture may include one or more graphic processing units. A graphic processing unit may include a plurality of scalar processors.

In some embodiments, the first image and the second image may be CT images. The first image and the second image may present different qualities with respect to CT number uniformity. For a CT image, CT numbers may indicate the attenuation distribution of the radiation beams that traverse the object. The CT number uniformity of a CT image may refer to the consistency of CT numbers of a homogeneous material (e.g., water, bone) in the image. In some embodiments, the CT number may be represented by the Hounsfield unit (HU). Merely by way of example, the CT number of water may be 0 HU, and the CT number of air may be −1000 HU.

In some embodiments, the second image may present a better CT number uniformity than the first image. The CT number uniformity of an image (e.g., the first image, the second image) may be expressed as an absolute value of the difference between the mean value of CT numbers of a homogeneous material (e.g., water, bone) in the center region of the image and the mean value of CT numbers of the homogeneous material in a corner region of the image. For example, the CT number uniformity of the second image may be within ±5 HU (the absolute value is 5 HU), and the CT number uniformity of the first image may be within ±7 HU (the absolute value is 7 HU). Therefore, the second image may present a better CT number uniformity than the first image.

In some embodiments, a corner region of the second image may present a better CT number uniformity than the corresponding corner region of the first image. For example, the CT number uniformity of the corner region of the second image may be within ±5 HU (the absolute value is 5 HU), and the CT number uniformity of the corresponding corner region of the first image may be within ±7 HU (the absolute value is 7 HU). Therefore, the corner region of the second image may present a better CT number uniformity than the corresponding corner region of the first image.

Alternatively, in some embodiments, the CT number uniformity of the first image (and/or the second image) or a region thereof may be described according to Equation (1):

$$u = \left(1 - \frac{CT_{max} - CT_{min}}{CT_{max} + CT_{min}}\right) \times 100\%, \qquad \text{Equation (1)}$$

where u represents the CT number uniformity of the first image or a region thereof, $CT_{max}$ represents the maximum CT number of a homogeneous material (e.g., water, bone) in the first image or a region thereof, and $CT_{min}$ represents the minimum CT number of the homogeneous material in the first image or a region thereof. For example, according to Equation (1), the CT number uniformity of a region (e.g., the center region) of the second image may be 90%, and the CT number uniformity of the corresponding region (e.g., the center region) of the first image may be 50%. Therefore, the region of the second image may present a better CT number uniformity than the corresponding region of the first image. As another example, according to Equation (1), the CT number uniformity of the second image may be 90%, and the CT number uniformity of the first image may be 50%. Therefore, the second image may present a better CT number uniformity than the first image.

In some embodiments, the difference of the CT number uniformity between the first image and the second image may be reflected in the brightness of the first image and the second image. For example, compared to the second image, the overall brightness of the first image may be relatively inconsistent, in that the average brightness of a part (e.g., a part on the left side) of the first image may be significantly lower than another part (e.g., a part on the right side) of the first image. The image illustrated in FIG. 15-A may be an exemplary first image, the image in FIG. 15-C may be an exemplary second image, and the image in FIG. 15-B may be an exemplary combined image that will be described in connection with the process 800 in FIG. 8. As shown in FIG. 15-A, the average brightness of the left region indicated by the arrow E is significantly lower than that of the right region indicated by the arrow F. As shown in FIG. 15-C, the average brightness of the left region indicated by the arrow E' is relatively close to that of the right region indicated by the arrow F'. Therefore, the second image in FIG. 15-C presents a better CT number uniformity than the first image in FIG. 15-A.

In some embodiments, the first image may have fewer artifacts than the second image. An artifact may be a distortion or error in an image that is irrelevant to the object being imaged. The artifacts in the first image and/or the second image may include, for example, streak artifacts, ring artifacts, motion artifacts, metal artifacts, or the like, or any combination thereof. As illustrated in FIG. 15-C, artifacts (e.g., streaks or dark bands) are present in the regions indicated by the arrows A', B', and C'. In contrast, the image in FIG. 15-A includes significantly reduced artifacts in corresponding regions indicated by the arrows A, B, and C. Similarly, the image in FIG. 14-A may be an exemplary first image, and the image in FIG. 14-C may be an exemplary second image. As illustrated in FIG. 14-C, artifacts are present in the regions indicated by the arrows A' and B'. In contrast, the image in FIG. 14-A includes significantly reduced artifacts in corresponding regions indicated by the arrows A and B.

In some embodiments, the first image may include better high frequency components than the second image. Additionally or alternatively, a corner region of the first image may include better low frequency components than the corresponding corner region of the second image. As used herein, a region of an image may be referred to as corresponding to a region of another image when each of the regions of the two images corresponds to a same part of an object represented in the images. A center region of the second image may include better low frequency components than the corresponding center region of the first image. A high frequency component of an image may be a component where the voxel/pixel values (e.g., gray values) change rapidly from one value to another. For example, a sharp edge present in an image may include more high frequency components than a region having a solid color. A low frequency component of an image may be a component where the voxel/pixel values (e.g., gray values) change slowly and gradually. For example, a region having a solid color may include more low frequency components than a sharp edge presented in the image.

The quality of the high frequency components and/or the low frequency components in a specific region of an image may be reflected in artifacts in the specific region. For example, the region indicated by the arrow A in FIG. 15-A (e.g., the first image) includes fewer artifacts than the region indicated by the arrow A' in FIG. 15-C (e.g., the second image), and thus the high frequency components in the region indicated by the arrow A may be considered better than the high frequency components in the region indicated by the arrow A'. As another example, the region indicated by the arrow C in FIG. 15-A (e.g., the first image) includes fewer artifacts than the region indicated by the arrow C' in FIG. 15-C (e.g., the second image), and thus the low frequency components in the region indicated by the arrow C may be considered better than the low frequency components in the region indicated by the arrow C'.

Figure 8:
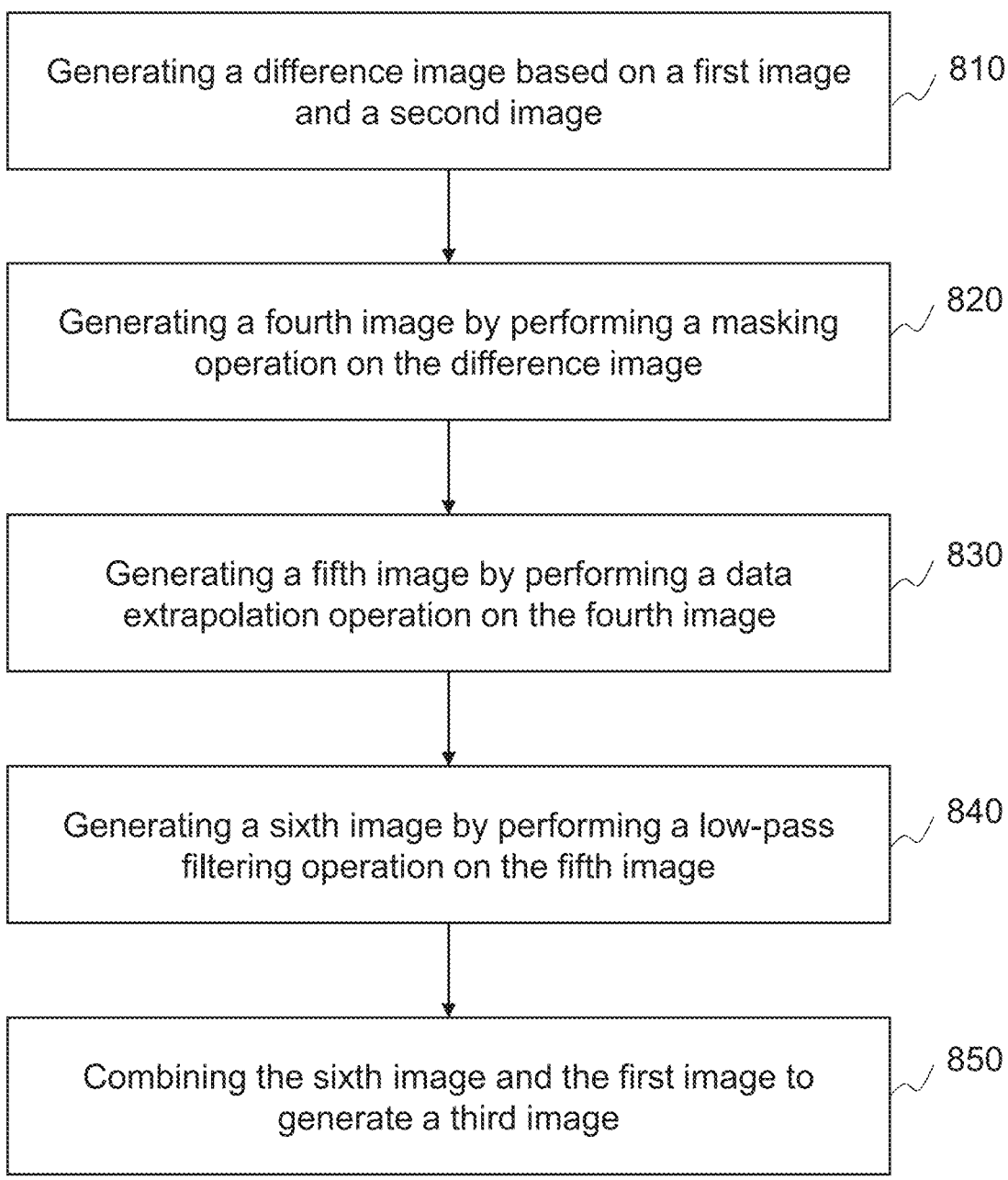
FIG. 8 is a flowchart illustrating an exemplary process for generating an image according to some embodiments of the present disclosure.

In 740, the processing device 120 (e.g., the image generation module 430) may generate a third image based on the first image and the second image. In some embodiments, the processing device 120 may generate the third image based on one or more operations including, for example, an image subtraction operation, a masking operation, a data extraction operation, a low-pass filtering operation, an image combination operation, etc. In some embodiments, the operation 740 may be implemented by executing one or more operations as illustrated in FIG. 8. The third image may combine the merits of the first image and the second image. The third image may present reduced artifacts and improved CT number uniformity. For example, the third image and the second image may present a better CT number uniformity than the first image. As another example, the third image and the first image may have fewer artifacts than the second image. More descriptions of the third image may be found elsewhere in the disclosure (e.g., FIG. 8 and the description thereof).

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, the process 700 may include an operation for pre-processing the projection data before 720. Exemplary pre-processing operation may include, for example, projection data normalization, projection data smoothing, projection data suppressing, projection data encoding (or decoding), preliminary denoising, etc.

FIG. 8 is a flowchart illustrating an exemplary process 800 for generating an image according to some embodiments of the present disclosure. The process 800 may be executed by the imaging system 100. For example, the process 800 may be stored in the storage device 140 and/or the storage 220 in the form of instructions (e.g., an application), and invoked and/or executed by the processing device 120 (e.g., the processor 210 illustrated in FIG. 2, or one or more modules in the processing device 120 illustrated in FIG. 4). The operations of the illustrated process presented below are intended to be illustrative. In some embodiments, the process 800 may be accomplished with one or more additional operations not described, and/or without one or more of the operations discussed. Additionally, the order in which the operations of the process 800 as illustrated in FIG. 8 and described below is not intended to be limiting. In some embodiments, the generation of the third image illustrated in the operation 740 of FIG. 7 may be implemented by performing one or more operations of the process 800.

Figure 9:
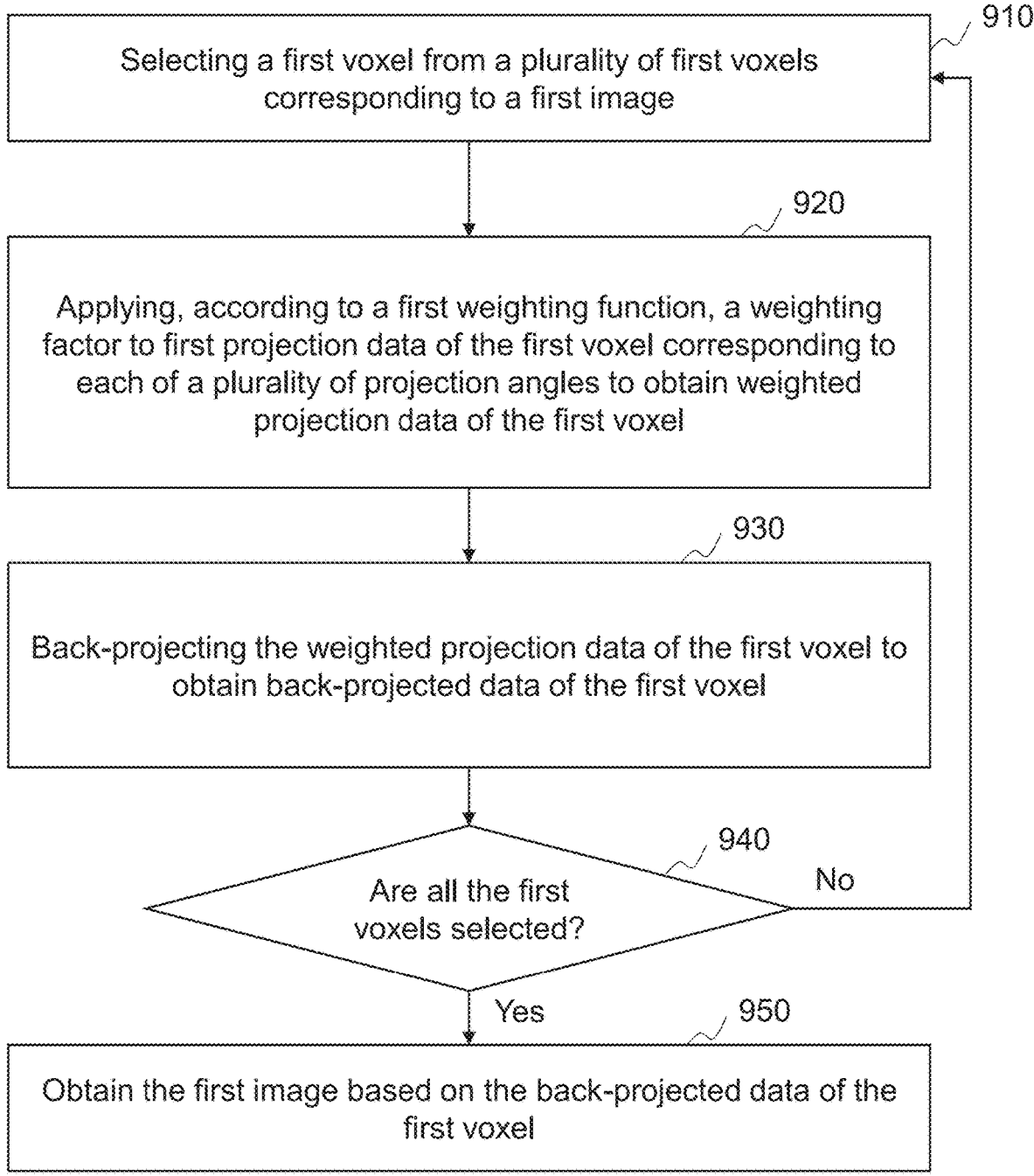
FIG. 9 is a flowchart illustrating an exemplary process for generating an image according to some embodiments of the present disclosure.

In 810, the image generation module 430 (e.g., the image subtraction unit 610) may generate a difference image based on a first image and a second image by, e.g., subtraction. In some embodiments, the image generation module 430 may obtain the first image and/or the second image of an object by executing one or more operations as illustrated in FIG. 7 or FIG. 9. For example, the first image and/or the second image may be obtained in connection with the operation 720 and/or the operation 730 as illustrated in FIG. 7. In some embodiments, the image generation module 430 may obtain the first image and the second image from the storage device 140, a storage module of the processing device 120, or an external storage device.

In some embodiments, the image generation module 430 may generate the difference image by subtracting one image from the other. For example, the image generation module 430 may generate the difference image by subtracting the first image from the second image. As another example, the image generation module 430 may generate the difference image by subtracting the second image from the first image. The image subtraction may refer to a subtraction operation between data (e.g., gray values) of corresponding pixels/voxels in the first image and the second image. As used herein, a pixel/voxel of an image may be referred to as corresponding to a pixel/voxel of another image when each of the pixels/voxels of the two images corresponds to a same part of an object represented in the images. For example, the image generation module 430 may subtract the gray value of a voxel in the corner region of the first image by the gray value of the corresponding voxel in the corresponding corner region of second image. As described elsewhere in the present disclosure, the first image may include better high frequency components than the second image, the corner region of the first image may include better low frequency components than the corresponding corner region of the second image, and the center region of the second image may include better low frequency components than the corresponding center region of the first image. To obtain a third image that combines the merits of the first image and the second image described above, the image generation module 430 may generate the difference image by subtracting the first image from the second image. By performing the subtraction operation and a low-pass filtering operation (will be described in detail in operation 840), the image generation module 430 may obtain the third image including better low frequency components in the center region compared to that of the first image and better high frequency components compared to that of the second image.

In 820, the image generation module 430 (e.g., the image masking unit 620) may generate a fourth image by performing a masking operation on the difference image. The difference image of the object may include four corner regions (e.g., the four corner regions 1004-1, 1004-2, 1004-3, and 1004-4 illustrated in FIG. 10) and a center region (e.g., the center region 1006 illustrated in FIG. 10). In some embodiments, the boundary between the four corner regions and the center region may be default settings of the imaging system 100, or may be adjustable under different situations. In some embodiments, the boundary may form a shape in a plane of the difference image. For example, as illustrated in FIG. 10, the boundary may form two cone surfaces in a plane of the image region 1002.

To perform the masking operation on the difference image, the image generation module 430 may provide a mask to the difference image. The mask may include a matrix (e.g., a two-dimensional matrix, a three-dimensional matrix), or a binary image in which the gray value of a pixel (or voxel) may be "0" or "1." Merely by way of example, the elements of the matrix corresponding to the corner regions of the difference image have the value of zero, and the elements of the matrix corresponding to the center region of the difference image have the value of one. By applying the mask on the difference image (e.g., making the mask multiply by the difference image), the image generation module 430 may reset the values of the pixels/voxels (e.g., gray values) in the four corner regions of the difference image to a default value (e.g., "0" for gray value), and the values of the pixels/voxels (e.g., gray values) at the center region of the difference image may remain unchanged.

For illustration purposes, the image in FIG. 13-A is provided as an exemplary fourth image according to some embodiments of the present disclosure. As illustrated in FIG. 13-A, the gray values of the pixels in the four corner regions indicated by the arrows A1, A2, A3, and A4 are set to be "0."

In 830, the image generation module 430 (e.g., the data extrapolation unit 630) may generate a fifth image by performing a data extrapolation operation on the fourth image. A data extrapolation operation may be a process in which the value of a specific data point is estimated based on the values of data points in the vicinity of the specific data point in space. By performing the data extrapolation operation on the fourth image, the image generation module 430 may assign the values of a pixel/voxel (e.g., gray value) in a corner region of the fourth image based on the values of pixels/voxels (e.g., gray values) in the center region of the fourth image. In some embodiments, the image generation module 430 may set the values of pixels/voxels in a corner region according to the values of pixels/voxels that are in the center region and closest to the corner region (e.g., at a boundary between the corner region and the center region). For example, the gray values of pixels on a vertical line segment in the corner region may be equal to the gray value of the pixel which is connected to the vertical line segment and at a boundary between the corner region and the center region.

In 840, the image generation module 430 (e.g., the low-pass filtering unit 640) may generate a sixth image by performing a low-pass filtering operation on the fifth image. The image generation module 430 may perform the low-pass filtering operation on the fifth image using a low-pass filter, such as, a Gaussian low-pass filter, a Butterworth low-pass filter, a Chebyshev low-pass filter, a 3D box filter (e.g., a 3×3×3 box filter), or the like, or any combination thereof. By performing the low-pass filtering operation to generate the sixth image, the image generation module 430 may reduce or remove the high frequency components of the fifth image and retain the low frequency components of the fifth image. In some embodiments, the image generation module 430 may perform one or more rounds of low-pass filtering on the fifth image. The parameters of the low-pass filtering in different rounds may be the same or different. For example, the cutoff frequencies of the low-pass filtering in different rounds may be different.

For illustration purposes, the image in FIG. 13-C is provided as an exemplary sixth image according to some embodiments of the present disclosure. Compared to the regions indicated by the arrows A1', A2', A3', and A4' in the fifth image illustrated in FIG. 13-B, high frequency components in the regions indicated by the arrows A1", A2", A3", and A4" are reduced or removed.

In 850, the image generation module 430 (e.g., the image combination unit 650) may combine the sixth image and the first image to generate a third image. The image combination may refer to a combination of data (e.g., gray value) of corresponding pixels/voxels in the sixth image and the first image. During the image combination, the image generation module 430 may apply one or more of various operations including, for example, an addition operation, a subtraction operation, a multiplication operation, a division operation, or any combination thereof. In some embodiments, the processing device 120 may combine the sixth image and the first image via a non-linear combination. The non-linear combination may be performed according to detected edge information and structure information in the sixth image and the first image. Structure information in an image may refer to high frequency components of the image. For example, the structure information in the sixth image or the first image of an object may correspond to a skeleton, an organ, etc., of the object.

The third image may show the same part of the object as the first image and the second image. For example, the third image may also have corner regions showing the corner part(s) of the object and a center region showing the center part of the object.

As described in connection with the operation 740 in the process 700, the third image may combine the merits of the first image and the second image. For example, the third image and the first image may have fewer artifacts than the second image. As illustrated in FIG. 14-A through FIG. 14-C, the regions indicated by the arrows A" and B" in FIG. 14-B (e.g., the third image) and the regions indicated by the arrows A and B in FIG. 14-A (e.g., the first image) present fewer artifacts than the regions indicated by the arrows A' and B' in FIG. 14-C (e.g., the second image).

Additionally, the third image and the second image may present a better CT number uniformity than the first image. As illustrated in FIG. 15-A (e.g., the first image), the average brightness of the left region indicated by the arrow E is significantly lower than that of the right region indicated by the arrow F. As illustrated in FIGS. 15-B and 15-C, the average brightness of the left region indicated by the arrow E" (or E') is relatively close to that of the right region indicated by the arrow F" (or F').

Further, the third image and the first image may present better high frequency components than the second image. As illustrated in FIG. 15-A (e.g., the first image), FIG. 15-B (e.g., the third image), and FIG. 15-C (e.g., the second image), regions indicated by the arrow A, A', or A" have several high frequency components. Compared to the region indicated by the arrow A', artifacts are reduced in the region indicated by the arrow A" and/or in the region indicated by the arrow A. Further, the corner region(s) in the third image and/or in the first image may present better low frequency components than the corner region(s) of the second image. As illustrated in FIGS. 15-A to 15-C, regions indicated by the arrow C, C', or C" have several low frequency components. Compared to the region indicated by the arrow C', artifacts are reduced in the region indicated by the arrow C" and/or in the region indicated by the arrow C. Similarly, the center region in the third image and/or in the second image may present better low frequency components than the center region in the first image. For example, low frequency components of the center region in the third image and/or in the second image may include few artifacts than low frequency components of the corresponding center region in the first image.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, the process 800 may include a storing operation for storing intermediate results (e.g., the difference image, the fourth image, the fifth image, etc.) during the generation of the third image.

FIG. 9 is a flowchart illustrating an exemplary process 900 for generating an image according to some embodiments of the present disclosure. The process 900 may be executed by the imaging system 100. For example, the process 900 may be stored in the storage device 140 and/or the storage 220 in the form of instructions (e.g., an application), and invoked and/or executed by the processing device 120 (e.g., the processor 210 illustrated in FIG. 2, or one or more modules in the processing device 120 illustrated in FIG. 4). The operations of the illustrated process presented below are intended to be illustrative. In some embodiments, the process 900 may be accomplished with one or more additional operations not described, and/or without one or more of the operations discussed. Additionally, the order in which the operations of the process 900 as illustrated in FIG. 9 and described below is not intended to be limiting. In some embodiments, the generation of the first image as illustrated in the operation 720 of FIG. 7 and/or the generation of the second image as illustrated in the operation 730 of FIG. 7 may be implemented by performing one or more operations of the process 900.

In 910, the image reconstruction module 420 may select a first voxel from a plurality of first voxels corresponding to a first image. In some embodiments, the first image may include a plurality of first voxels.

In 920, the image reconstruction module 420 (e.g., the weighting unit 510) may apply, according to a first weighting function, a weighting factor to first projection data of the first voxel corresponding to each of a plurality of projection angles to obtain weighted projection data of the first voxel.

In some embodiments, the weighting factors applied to the first projection data of the first voxel according to different projection angles may be different. As illustrated in FIG. 11, the radiation source may scan an object 1102 along a circular trajectory 1103. When the radiation source is located at position 1101 (corresponding to the projection angle of 13), a radiation ray 1104 (e.g., an X-ray) may be emitted from the radiation source to a detector 1105 (e.g., a flat detector). The radiation ray 1104 may pass through a voxel 1106 (e.g., the first voxel) of the object 1102 and form a projection point 1107 on the detector 1105. The detector 1105 may be associated with a local coordinate system defined by the origin O' and the u-axis and the v-axis. The direction of the v-axis may be parallel to the direction of the Z-axis of the XYZ coordinate system as illustrated. The origin of the local coordinate system O' may be in the plane of the origin O. When the radiation source moves along the circular trajectory, the voxel 1106 may be radiated by the radiation source from a plurality of projection angles, thus forming different projection points on the detector 1105. In some embodiments, the weighting factor applied to the first projection data corresponding to a specific projection angle may be associated with the position of the projection point on the detector 1105 at the specific projection angle. For example, a first weighting factor associated with a first projection point located at the center point of the detector 1105 may be greater than a second weighting factor associated with a second projection point located at an edge point of the detector 1105.

For better understanding the weighting factors applied to the first projection data, an exemplary illustration is provided in the following, which is not intended to be limiting.

Figure 12:
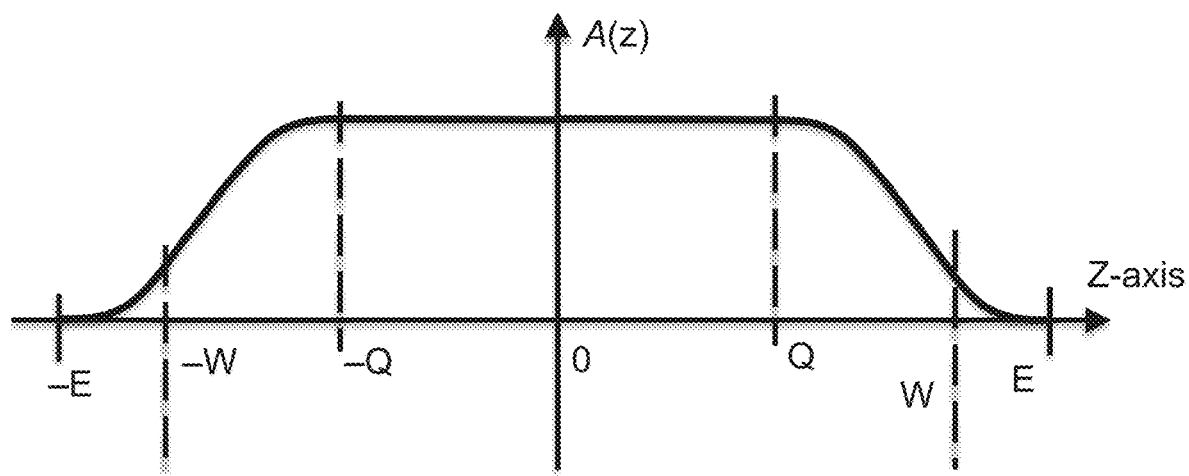
FIG. 12 is a schematic diagram illustrating an exemplary aperture weighting function according to some embodiments of the present disclosure.

The weighting function (e.g., the first weighting function described herein) may be an aperture weighting function as illustrated in FIG. 12. In some embodiments, the aperture weighting function may be expressed as Equation (2):

$$A(z) = \begin{cases} \sin^2\left(\frac{\pi}{2}\frac{E-z}{E-Q}\right), & Q < z < E \\ 1.0, & -Q \leq z \leq Q \\ \sin^2\left(\frac{\pi}{2}\frac{E+z}{E-Q}\right), & -E < z < -Q \end{cases} \quad \text{Equation (2)}$$

where A(z) represents the aperture weighting function, z represents the position of the projection point at the detector 1105 along the v-axis or the Z-axis illustrated in FIG. 11, denoted as a value in the Z-axis in FIG. 12, Q represents a first parameter of the aperture weighting function A(z), and E represents a second parameter of the aperture weighting function A(z). It shall be noted that, when the projection point is located within a center range of the detector 1105 (i.e., −Q≤z≤Q), the value of the aperture weighting function A(z) is a constant. When the projection point is located beyond the center range of the detector 1105, the value of the aperture weighting function A(z) decreases with the increase of the distance between the projection point and the center point 0 illustrated in FIG. 12. The first parameter Q may be associated with the dimension of the center range of the detector, and the second parameter E may be associated with the dimension of the descending trend of the aperture weighting function A(z) beyond the center range. In some embodiments, the first parameter Q and the second parameter E may be in proportional to the width W of the detector 1105. For example, the value of Q may be 0.6*W, and the value of E may be 1.1*W. For brevity, the values of (Q,E) may be expressed as (0.6*W, 1.1*W). As another example, the value of Q may be 1.0*W, the value of E may be 1.1*W, and the values of (Q,E) may be expressed as (1.0*W, 1.1*W).

The assignment of different values of the first parameter Q and the second parameter E may generate different weighting functions, such as, the first weighting function and the second function illustrated in connection with the operations 720 and 730 in the process 700. The values of the first parameter Q and the second parameter E may affect the qualities of the first image and the second image. In some embodiments, the first weighting function and the second weighting function may be assigned the same value of the second parameter E Additionally, the first weighting function may be assigned a smaller value of the first parameter Q than the second weighting function. Accordingly, as described elsewhere in the disclosure, the first image may include fewer artifacts and better high frequency components than the second image. Further, a corner region of the first image may include better low frequency components than the corresponding corner region of the second image. Moreover, the second image may present a better CT number uniformity than the first image. The center region of the second image may include better low frequency components than the corresponding center region of the first image.

For example, in FIGS. 14-A and 14-C, the values of (Q,E) assigned in reconstructing the image in FIG. 14-A (e.g. the first image) are (0.0, 1.1), and the values of (Q,E) assigned in reconstructing the image in FIG. 14-C (e.g., the second image) are (1.0, 1.1). As shown in FIG. 14-A, compared to the regions indicated by the arrows A' and B' in FIG. 14-C, artifacts are reduced in the regions indicated by the arrows A and B in FIG. 14-A.

As another example, in FIGS. 15-A and 15-C, the values of (Q,E) assigned in reconstructing the image in FIG. 15-A (e.g. the first image) are (0.0, 1.1), and the values of (Q,E) assigned in reconstructing the image in FIG. 15-C (e.g., the second image) are (1.0, 1.1). As shown in FIG. 15-A, the average brightness of the left region indicated by the arrow E is significantly lower than the right region indicated by the arrow F. As shown in FIG. 15-C, the average brightness of the left region indicated by the arrow E' is relatively close to the right region indicated by the arrow F'. Therefore, the image in FIG. 15-C presents a better CT number uniformity than the image in FIG. 15-A.

In some embodiments, the weighting factor applied to the first projection data corresponding to a specific projection angle may be determined based on one or more values of the aperture weighting function A(z). For example, the weighting factor for the first projection data of the first voxel may be a normalized value of a first value and a second value of the aperture weighting function A(z). In some embodiments, the normalization may provide a good CT number uniformity for the first image. In some embodiments, the normalization may be a linear normalization in which the weight may be described according to Equation (3):

$$w = w1/(w1+w2), \quad \text{Equation (3)}$$

where w represents the weighting factor applied to the first projection data of the first voxel corresponding to a projection angle, w1 represents the first value of the aperture weighting function A(z), and w2 represents the second value of the aperture weighting function A(z).

Alternatively, the normalization may be described according to Equation (4):

$$w = w1/(w1+a^2 w2), \quad \text{Equation (4)}$$

where a represents a coefficient which may de determined by the weighting unit 510 or set manually by a user.

In some embodiments, the first value w1 of the aperture weighting function A(z) may be associated with a first projection point on a detector where radiation from the radiation source at the projection angle strikes and the second value w2 of the aperture weighting function A(z) may be associated with a second projection point on the detector where radiation from the radiation source at an opposite projection angle strikes. The difference between the opposite projection angle and the projection angle may be 180° or −180°. For example, as illustrated in FIG. 11, when the radiation source is located at the position 1101, the projection angle is β. The radiation ray 1104 passing through the voxel 1106 forms the first projection point (i.e., the projection point 1107) on the detector 1105. The opposite projection angle of the projection angle β is 180°+β or β−180°. The position of the radiation source at the opposite projection angle (e.g., the position 1109 as shown in FIG. 11) and the position 1101 are symmetrical with respect to the origin O illustrated in FIG. 11. When the radiation source is located at the position corresponding to the opposite projection angle, a radiation ray passing through the voxel 1106 forms the second projection point (not shown) on the detector 1105. As described above, the first projection point and the second projection point may correspond to the first value w1 of the first weighting function and the second value w2 of the first weighting function, respectively.

In 930, the image reconstruction module 420 (e.g., the back projection unit 520) may back-project the weighted projection data of the first voxel to obtain back-projected data of the first voxel. The back-projected data of the first voxel may refer to the voxel value of the first voxel. In some embodiments, the image reconstruction module 420 may determine a BP value of the first voxel for each of the plurality of projection angles. The image reconstruction module 420 may add up all BP values of the first voxel, each corresponding to one of the plurality of projection angles, to obtain the back-projected data of the first voxel.

In 940, the image reconstruction module 420 may determine whether all the first voxels corresponding to the first image have been selected. If not all the first voxels are selected, the process 900 may return back to the operation 910 to select a new first voxel from the rest first voxels, and repeat the operations 920 and 930. If all the first voxels have been selected, the process 900 may proceed to the operation 950 to obtain the first image based on the back-projected data of the first voxel.

In some embodiments, the image reconstruction module 420 may be implemented on a parallel hardware architecture. The parallel hardware architecture may include a plurality of processing threads (e.g., processing thread "A" and processing thread "B") to execute operations concurrently. The processing thread "A" may perform at least one of the operations illustrated in FIG. 9 to generate the first image, and concurrently the processing thread "B" may perform at least one of corresponding operations illustrated in FIG. 9 to generate the second image.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, before the operation 930, the process 900 may include a convolution operation performed on the weighted projection data of the first voxel (e.g., calculating the convolution of the weighted projection data of the first voxel and a filter function (e.g., an S-L filter function)) to obtain enhanced edge sharpness in the first image. As another example, the image reconstruction module 420 may adjust the values of (Q,E) in the first weighting function and/or the second weighting function according to the object to be reconstructed. For example, for the head and a breast of a patient, the processing device 120 may apply different values of (Q,E) in the first weighting function and/or the second weighting function.

EXAMPLES

The following examples are provided for illustration purposes, and are not intended to limit the scope of the present disclosure.

FIG. 13-A is an exemplary image according to some embodiments of the present disclosure. The image is a CT image generated based on the projection data of an object (e.g., a breast). The arrows A1, A2, A3, and A4 indicate portions of the image corresponding to corner parts of the object. The arrow B indicates a portion of the image corresponding to a center part of the object. The gray values of the pixels in the portions of the image indicated by the arrows A1, A2, A3, and A4 are "0."

FIG. 13-B is an exemplary image generated based on a data extrapolation operation performed on FIG. 13-A according to some embodiments of the present disclosure. The arrows A1', A2', A3', and A4' indicate portions of the image corresponding to corner parts of the object. The arrow B' indicates a portion of the image corresponding to a center part of the object.

FIG. 13-C is an exemplary image generated based on a low-filtering operation performed on FIG. 13-B according to some embodiments of the present disclosure. The arrows A", A2", A3", and A4" indicate portions of the image corresponding to corner parts of the object. The arrow B" indicates a portion of the image corresponding to a center part of the object.

FIGS. 14-A to 14-C illustrate three exemplary images according to some embodiments of the present disclosure. The three images are sagittal CT images related to the chest reconstructed according to an aperture weighting function with different values of (Q,E). The values of (Q,E) assigned in reconstructing the image in FIG. 14-A are (0.0, 1.1), and the values of (Q,E) assigned in reconstructing the image in FIG. 14-C are (1.0, 1.1). The image in FIG. 14-B was generated based on the image in FIG. 14-A and the image in FIG. 14-C by performing the process 800 as illustrated in FIG. 8.

FIGS. 15-A to 15-C illustrate three exemplary images according to some embodiments of the present disclosure. The three images are axial CT images related to the chest reconstructed according to an aperture weighting function with different values of (Q,E). The values of (Q,E) assigned in reconstructing the image in FIG. 15-A are (0.0, 1.1), and the values of (Q,E) assigned in reconstructing the image in FIG. 15-C are (1.0, 1.1). The image in FIG. 15-B was generated based on the image in FIG. 15-A and the image in FIG. 15-C by performing the process 800 illustrated in FIG. 8.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by the present disclosure and are within the spirit and scope of the exemplary embodiments of the present disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer-readable media having computer readable program code embodied thereon.

A computer readable signal medium may include a propagated data signal with computer readable program code embodied therein, for example, in baseband or as part of a carrier wave. Such a propagated signal may take any of a variety of forms, including electromagnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object-oriented programming language such as Java, Scala, Smalltalk, Eiffel, JADE, Emerald, C++, C #, VB. NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations, therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software-only solution, for example, an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

We claim:

1. A system, comprising:
at least one storage device including a set of instructions; and
at least one processor in communication with the at least one storage device, wherein when executing the instructions, the at least one processor is configured to cause the system to perform operations including:
obtaining projection data of an object, wherein the projection data is generated by a scanner via scanning the object which is located in a scanning region of the scanner;
generating, based on a first weighting function, a first image corresponding to the object by back-projecting the projection data, wherein the first image includes a first region corresponding to at least a part of the object;

generating, based on a second weighting function, a second image corresponding to the object by back-projecting the projection data, wherein the second image includes a second region corresponding to the at least part of the object, and the second region of the second image presenting a better CT number uniformity than the first region of the first image; and generating a third image of the object based on the first image and the second image.

2. The system of claim 1, wherein the first image has fewer artifacts than the second image.

3. The system of claim 1, wherein the first image includes better high frequency components than the second image.

4. The system of claim 1, wherein the scanner further includes:
a radiation source configured to scan the object along a circular trajectory covering an angle range of 360° to produce the projection data.

5. The system of claim 4, wherein
the at least part of the object is radiated by the radiation source at an angle range less than 360°, and
the first region of the first image includes better low frequency components than the second region of the second image.

6. The system of claim 1, wherein
the scanning region of the scanner includes a first scanning region and a second scanning region, and
the first weighting function includes a first weighting factor and a second weighting factor, the first weighting factor relating to a first angle range of the first scanning region, the second weighting factor relating to a second angle range of the second scanning region, wherein
the first weighting factor is assigned to a first part of the projection data corresponding to the first scanning region;
the second weighting factor is assigned to a second part of the projection data corresponding to the second scanning region; and
the first weighting factor is different from the second weighting factor.

7. The system of claim 6, wherein
the first scanning region is a corner part of the scanning region and the first part of the projection data is generated from a first set of radiation beams of the scanner that pass through a first corner part of the object; and
the second scanning region is a center part of the scanning region and the second part of the projection data is generated from a second set of radiation beams of the scanner that pass through a center part of the object.

8. The system of claim 1, wherein
the scanning region of the scanner includes a third scanning region and a fourth scanning region, and
the second weighting function includes a third weighting factor and a fourth weighting factor, the third weighting factor relating to a third angle range of the third scanning region, the fourth weighting factor relating to a fourth angle range of the fourth scanning region, wherein
the third weighting factor is assigned to a third part of the projection data corresponding to the third scanning region in which a second corner part of the object is located;

the fourth weighting factor is assigned to a fourth part of the projection data corresponding to the fourth scanning region in which a center part of the object is located; and
the third weighting factor is different from the fourth weighting factor.

9. The system of claim 8, wherein the second region of the second image corresponds to the second corner part of the object.

10. The system of claim 1, wherein to generate a third image, the at least one processor is configured to cause the system to perform the operations including:
generating a difference image of the first image and the second image by subtraction; and
determining the third image based on the difference image and the first image.

11. A method for image generation implemented on at least one machine each of which includes at least one processor and at least one storage device, the method comprising:
obtaining projection data of an object, wherein the projection data is generated by a scanner via scanning the object which is located in a scanning region of the scanner;
generating, based on a first weighting function, a first image corresponding to the object by back-projecting the projection data, wherein the first image includes a first region corresponding to at least a part of the object;
generating, based on a second weighting function, a second image corresponding to the object by back-projecting the projection data, wherein the second image includes a second region corresponding to the at least part of the object, and the second region of the second image presenting a better CT number uniformity than the first region of the first image; and
generating a third image of the object based on the first image and the second image.

12. The method of claim 11, wherein the first image has fewer artifacts than the second image.

13. The method of claim 11, wherein the first image includes better high frequency components than the second image.

14. The method of claim 11, wherein the scanner further includes:
a radiation source configured to scan the object along a circular trajectory covering an angle range of 360° to produce the projection data.

15. The method of claim 14, wherein
the at least part of the object is radiated by the radiation source at an angle range less than 360°, and
the first region of the first image includes better low frequency components than the second region of the second image.

16. The method of claim 14, wherein
the scanning region of the scanner includes a first scanning region and a second scanning region, and
the first weighting function includes a first weighting factor and a second weighting factor, the first weighting factor relating to a first angle range of the first scanning region, the second weighting factor relating to a second angle range of the second scanning region, wherein
the first weighting factor is assigned to a first part of the projection data corresponding to the first scanning region;
the second weighting factor is assigned to a second part of the projection data corresponding to the second scanning region; and the first weighting factor is different from the second weighting factor.

17. The method of claim 16, wherein
the first scanning region is a corner part of the scanning region and the first part of the projection data is generated from a first set of radiation beams of the scanner that pass through a first corner part of the object; and
the second scanning region is a center part of the scanning region and the second part of the projection data is generated from a second set of radiation beams of the scanner that pass through a center part of the object.

18. The method of claim 11, wherein
the scanning region of the scanner includes a third scanning region and a fourth scanning region, and
the second weighting function includes a third weighting factor and a fourth weighting factor, the third weighting factor relating to a third angle range of the third scanning region, the fourth weighting factor relating to a fourth angle range of the fourth scanning region, wherein
the third weighting factor is assigned to a third part of the projection data corresponding to the third scanning region in which a second corner part of the object is located;
the fourth weighting factor is assigned to a fourth part of the projection data corresponding to the fourth scanning region in which a center part of the object is located; and
the third weighting factor is different from the fourth weighting factor.

19. The method of claim 18, wherein the second region of the second image corresponds to the second corner part of the object.

20. A non-transitory computer readable medium embodying a computer program product, the computer program product comprising instructions configured to cause a computing device to perform operations including:
obtaining projection data of an object, wherein the projection data is generated by a scanner via scanning the object which is located in a scanning region of the scanner;
generating, based on a first weighting function, a first image corresponding to the object by back-projecting the projection data, wherein the first image includes a first region corresponding to at least a part of the object;
generating, based on a second weighting function, a second image corresponding to the object by back-projecting the projection data, wherein the second image includes a second region corresponding to the at least part of the object, and the second region of the second image presenting a better CT number uniformity than the first region of the first image; and
generating a third image of the object based on the first image and the second image.

* * * * *